United States Patent
Saab et al.

(10) Patent No.: US 9,814,510 B2
(45) Date of Patent: *Nov. 14, 2017

(54) APPARATUS AND METHODS FOR ACCESSING AND DILATING BONE STRUCTURES USING A NARROW GAUGE CANNULA

(71) Applicants: Mark A. Saab, Lowell, MA (US); Michael D. Barbere, Dunstable, MA (US)

(72) Inventors: Mark A. Saab, Lowell, MA (US); Michael D. Barbere, Dunstable, MA (US)

(73) Assignee: Nordson Corporation, Westlake, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/172,408

(22) Filed: Jun. 3, 2016

(65) Prior Publication Data

US 2016/0278837 A1    Sep. 29, 2016

Related U.S. Application Data

(63) Continuation of application No. 14/005,622, filed as application No. PCT/US2012/000162 on Mar. 24, 2012, now Pat. No. 9,358,372.

(60) Provisional application No. 61/465,893, filed on Mar. 25, 2011.

(51) Int. Cl.
| | |
|---|---|
| *A61B 17/88* | (2006.01) |
| *A61M 25/01* | (2006.01) |
| *A61M 29/02* | (2006.01) |
| *A61M 25/10* | (2013.01) |

(52) U.S. Cl.
CPC ...... *A61B 17/8855* (2013.01); *A61M 25/0144* (2013.01); *A61M 25/1036* (2013.01); *A61M 29/02* (2013.01); *A61M 25/1034* (2013.01); *A61M 2025/015* (2013.01); *A61M 2025/1004* (2013.01)

(58) Field of Classification Search
CPC ...... A61B 17/8855; A61M 2025/0024; A61M 25/10
See application file for complete search history.

(56) References Cited

U.S. PATENT DOCUMENTS

| | | |
|---|---|---|
| 624,811 A | 5/1899 | Hunt et al. |
| 3,779,239 A | 12/1973 | Fischer et al. |
| 4,261,339 A | 4/1981 | Hanson et al. |
| 4,406,656 A | 9/1983 | Hattler et al. |

(Continued)

FOREIGN PATENT DOCUMENTS

EP    0223176    5/1987

OTHER PUBLICATIONS

European Search Report dated Oct. 19, 2015 in corresponding European Application No. 12765759.1.

(Continued)

*Primary Examiner* — Andrew Yang
(74) *Attorney, Agent, or Firm* — Baker & Hostetler LLP

(57) ABSTRACT

Systems, apparatus and methods are disclosed for medical treatment comprising bone access and dilatation and/or cavity creation or enlargement using a narrow gauge, preferably 11-gauge or smaller, cannula wherein a catheter/expandable element assembly meeting medical protocols is designed, adapted and fabricated to fit through the interior of the associated 11-gauge or smaller cannula.

28 Claims, 14 Drawing Sheets

(56) References Cited

U.S. PATENT DOCUMENTS

| | | |
|---|---|---|
| 4,422,447 A | 12/1983 | Schiff |
| 4,734,093 A | 3/1988 | Bonello et al. |
| 4,846,174 A | 7/1989 | Willard et al. |
| 4,969,888 A | 11/1990 | Scholten et al. |
| 5,108,404 A | 4/1992 | Scholten et al. |
| 5,163,989 A | 11/1992 | Campbell et al. |
| 5,290,306 A | 3/1994 | Trotta et al. |
| 5,295,994 A | 3/1994 | Bonutti |
| 5,331,975 A | 7/1994 | Bonutti |
| 5,342,301 A | 8/1994 | Saab |
| 5,352,199 A | 10/1994 | Tower |
| 5,361,752 A | 11/1994 | Moll et al. |
| 5,411,477 A | 5/1995 | Saab |
| 5,492,532 A | 2/1996 | Ryan et al. |
| 5,499,973 A | 3/1996 | Saab |
| 5,569,195 A | 10/1996 | Saab |
| 5,624,392 A | 4/1997 | Saab |
| 5,741,282 A | 4/1998 | Anspach, III et al. |
| 5,766,151 A | 6/1998 | Valley et al. |
| 5,772,681 A | 6/1998 | Leoni |
| 5,795,325 A | 8/1998 | Valley et al. |
| 5,797,878 A | 8/1998 | Bleam |
| 5,827,289 A | 10/1998 | Reiley |
| 5,972,015 A | 10/1999 | Scribner et al. |
| 6,013,085 A | 1/2000 | Howard |
| 6,048,346 A | 4/2000 | Reiley et al. |
| 6,066,154 A | 5/2000 | Reiley et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,383,190 B1 | 5/2002 | Preissman |
| 6,582,446 B1 | 6/2003 | Marchosky |
| 6,607,544 B1 | 8/2003 | Boucher et al. |
| 6,613,054 B2 | 9/2003 | Scribner et al. |
| 6,719,773 B1 | 4/2004 | Boucher et al. |
| 6,780,183 B2 | 8/2004 | Jimenez, Jr. et al. |
| 6,979,341 B2 | 12/2005 | Scribner et al. |
| 7,261,720 B2 | 8/2007 | Stevens et al. |
| 7,488,337 B2 | 2/2009 | Saab et al. |
| 7,722,624 B2 | 5/2010 | Boucher et al. |
| 8,177,744 B2 | 5/2012 | Saab et al. |
| 8,216,182 B2 | 7/2012 | Saab et al. |
| 8,394,056 B2 | 3/2013 | Saab et al. |
| 8,454,646 B2 | 6/2013 | Saab et al. |
| 8,454,647 B2 | 6/2013 | Saab et al. |
| 2001/0007938 A1 | 7/2001 | Long |
| 2002/0156482 A1 | 10/2002 | Scribner et al. |
| 2002/0161373 A1 | 10/2002 | Osorio et al. |
| 2002/0183778 A1 | 12/2002 | Reiley et al. |
| 2003/0045869 A1 | 3/2003 | Ryan |
| 2003/0050702 A1 | 3/2003 | Berger |
| 2008/0140084 A1 | 6/2008 | Osorio et al. |
| 2009/0177236 A1 | 7/2009 | Saab et al. |
| 2010/0298832 A1 | 11/2010 | Lau et al. |
| 2013/0345765 A1 | 12/2013 | Brockman et al. |

OTHER PUBLICATIONS

International Search Report dated Jul. 27, 2012 in corresponding PCT Application No. PCT/US2012/00162.

APPARATUS AND METHODS FOR ACCESSING AND DILATING BONE STRUCTURES USING A NARROW GAUGE CANNULA

CROSS REFERENCE TO RELATED APPLICATIONS

This is a Continuation of U.S. Ser. No. 14/005,622 filed Sep. 17, 2013, now U.S. Pat. No. 9,358,372, which was a Sec. 371 application based on international application PCT/US 12/00162 filed Mar. 24, 2012, which claims the benefit of the filing date of U.S. Provisional Application Ser. No. 61/465,893 filed Mar. 25, 2011.

FIELD OF THE INVENTION

The present invention relates generally to systems, apparatus and methods for stabilizing bone structures by accessing and dilating such bone structures using a narrow gauge cannula, for example in surgically treating bone deformities and bones suffering from or predisposed to fracture or to collapse, particularly spinal fractures such as those commonly resulting from osteoporosis. The present invention further relates to systems, apparatus and methods for delivering a curable, stabilizing material into a bone structure, such as a vertebral body, through a narrow gauge cannula.

In some invention embodiments, an inflatable element is inserted into an interior region, cavity or passage of a damaged, collapsed, or deformed bone segment using a narrow gauge cannula; and, thereafter the inflatable element is inflated to form, enlarge or support the interior bone region thereby to effect a desirable realignment of the damaged bone segment with adjacent bone portions and to create a cavity. In at least some embodiments of this invention, following the dilatation step, the inflatable element may be collapsed and withdrawn from the interior bone region. A suitable bone support material may then be introduced into the dilated bone cavity. In some embodiments, the inflatable element may be left in place, and the cavity or the interior of the element may be filled with a suitable support material. The present invention has particular application in, but is not limited to, treatment of vertebral body compression fractures.

GENERAL BACKGROUND OF THE INVENTION

A number of diseases, illnesses and other medical conditions are treatable at least in part by dilatation of a bone, tissue or duct. For example, medical conditions and/or physical injuries can lead to or predispose a bone to deformity, such as a fracture. A familiar example is osteoporosis, in which bones lose calcium and break more easily. The human spinal column, comprised of interconnected vertebrae or vertebral bodies, has proven to be especially susceptible to the effects of osteoporosis. A vertebral body weakened by osteoporosis can fracture from a fall, or simply during routine activities. When a vertebral body fractures, it can collapse and change the shape of the spine. The damaged portion of the spine becomes shorter, and the rest of the spine above the broken vertebral body bends forward. As additional vertebral fractures occur, the spine shortens further, increasingly forcing the individual into a hunched-over posture.

As taught by U.S. Pat. No. 6,248,110 (Reiley et al.), U.S. Pat. No. 6,235,043 (Reiley et al.) and U.S. Pat. No. 6,066, 154 (Reiley et al.), each of which is incorporated herein in its entirety by reference, it is known in the art to use expandable bodies, such as a balloon element, to treat certain bone conditions, resulting from osteoporosis, avascular necrosis, bone cancer and the like, that predispose a bone to, or lead to, fracture or collapse. A particularly common application is in the treatment of vertebral body compression fractures resulting from osteoporosis.

Typical treatment of such conditions includes a series of steps which a surgeon or health care provider can perform to form a cavity in an interior region of pathological bone, including but not limited to osteoporotic bone, osteoporotic fractured metaphyseal and epiphyseal bone, osteoporotic vertebral bodies, fractured osteoporotic vertebral bodies, fractures of vertebral bodies due to tumors especially round cell tumors, avascular necrosis of the epiphyses of long bones, especially avascular necrosis of the proximal femur, distal femur and proximal humerus and defects arising from endocrine conditions.

The method typically further includes the steps of making an incision in the skin (usually one incision, but a second small incision may also be required if a suction egress is used) followed by the placement of a guide pin which is passed through the soft tissue down to and into the bone.

The method of the Reiley '154 patent, for example, further includes the steps of drilling the bone to be treated to form a cavity or passage in the bone, following which an inflatable balloon-like device is inserted into the cavity or passage where it is inflated. The inflation of the inflatable device causes a compacting of the cancellous bone and bone marrow against the inner surface of the cortical wall of the bone to further enlarge the cavity or passage. The inflatable device is then deflated and then is completely removed from the bone. The art further teaches that a smaller inflatable device (a starter balloon) can be used initially, if needed, to initiate the compacting of the bone marrow and to commence the formation of the cavity or passage in the cancellous bone and marrow. After this has occurred, a larger, inflatable device can be inserted into the cavity or passage to further compact the bone marrow in all directions.

Next in accordance with Reiley '154, a flowable biocompatible filling material, such as methylmethacrylate cement or a synthetic bone substitute, is directed into the bone cavity or passage that has been formed and enlarged, and the filling material is allowed to set to a hardened condition to provide ongoing structural support for the bone. Following this latter step, the insertion instruments are removed from the body and the incision in the skin is covered with a bandage.

A related U.S. Pat. No. 6,048,346 (Reiley et al.), which is also incorporated herein in its entirety by reference, teaches an improved mechanical bone cement injection assembly, which is described as constituting an improvement over prior art devices that operated "similar to a household caulking gun" in that it facilitates greater control over the placement of cement and other flowable liquids into an interior region of a bone.

Another inflatable apparatus intended for deployment into interior body regions is described in U.S. Pat. No. 5,972,015 (Scribner et al.), which is also incorporated herein in its entirety by reference. The Scribner '015 patent describes a catheter tube extending along a first axis in conjunction with an expandable structure having an expanded geometry oriented about a second axis, not aligned with the first axis, so as to treat an asymmetrically-shaped interior body region or where the access channel cannot be aligned with the body region to be treated. A particular application of this technology is stated to be for the fixation of fractures or other osteoporotic and non-osteoporotic conditions of human and animal bones, specifically for treating a human lumbar vertebra.

Two somewhat earlier patents describing similar apparatus and methods for treating vertebral body compression fractures and the like using an inflatable balloon-like element inserted into the bone cavity are U.S. Pat. No. 5,108,404 (Scholten et al.) and U.S. Pat. No. 4,969,888 (Scholten et al.), each of which is also incorporated herein in its entirety by reference.

In additional embodiments of known technologies for treating bone structures, U.S. Pat. No. 6,613,054 (Scribner et al.) and U.S. Pat. No. 6,241,734 (Scribner et al.), each of which is incorporated herein in its entirety by reference, describe systems and methods for advancing a tamping instrument through a cannula that has been deployed to establish a subcutaneous channel into bone. Material is introduced into the bone through the cannula, and the tamping instrument is used to move material in the cannula into the bone.

Numerous problems remain, however, with the prior art systems and methods. For successful expansion of a fractured vertebral body, an expandable element inserted into the vertebral cavity must be capable of being inflated to a relatively large working diameter of about 12 mm-25 mm, starting with a relatively short balloon working length, e.g., about 10 mm-25 mm, sized to fit inside the vertebral cavity, at very high working pressures on the order of 200-450 psi or higher. Use of lower inflation pressure in such applications may result in only a partial, incomplete expansion of a fractured vertebral body. When that partially-expanded vertebral body is subsequently filled with cement or comparable material, which then hardens, there is a permanent remaining spinal deformity at that vertebral body. Not only must the expandable/inflatable element in the vertebral cavity be capable of inflation to very high pressure without rupture in order to fully expand a collapsed/fractured vertebral body, in addition the inflated element must resist puncture by hard, sharp cancellous bone and surface irregularities around the outer edges of the vertebral cavity.

One possible approach to improve the strength of the balloon-like elements to make them better able to withstand very high inflation pressures would be to use thicker balloon walls and/or to make these elements out of stiffer, stronger materials. There are several reasons, however, why these seemingly straightforward solutions have not proven successful in practice. One is the need to limit the balloon wall thickness and the need to maintain balloon wall flexibility to facilitate access to, and withdrawal from, a bone cavity.

In treating a vertebral fracture, for example, the vertebral cavity is typically accessed by drilling a small hole and locating a short, hollow, metallic tubular element (i.e., a hollow sleeve or cannula) through the left or right pedicle portion (or sometimes both) of the vertebral arch (see, e.g., FIG. 2 of U.S. Pat. No. 5,972,015, which shows the left and right pedicle portions 42 of vertebral arch 40, and FIG. 6 of the same patent which shows an access hole for catheter tube 50 and expandable structure 56 through one pedicle portion 42 into the interior volume 30 of reticulated cancellous, or spongy, bone 32). Because pedicle portion 42 shown in FIGS. 2 and 6 of the Scribner '015 patent is relatively small and is itself readily susceptible to fracture if its structural integrity is impaired by too large a hole, it is crucial to keep the diameter of the hole, therefore also of the cannula, to a minimum, typically no larger than about 4-5 mm. Indeed, as taught hereinafter, it has become desirable based on current medical practice to use an opening made by an 11-gauge needle with a diameter of only about 0.121 inches (about 3.06 mm) or less, thereby requiring the use of an 11-gauge needle cannula. The cannula helps to protect surrounding bone portions from abrasion and from expansion forces while inserting or removing the catheter shaft or while inflating the balloon element that is bonded to the distal end of the catheter shaft.

Because of the narrow interior diameter of the cannula used in these applications, it was typical to fold or wrap the balloon-like element relatively tightly at the distal end of an associated catheter shaft in order to keep the maximum diameter of the unit at the balloon end small enough to fit through the cannula of a small-diameter pedicle hole. An expandable element fabricated with relatively thick walls and/or made from a relatively stiff, less flexible material might be inflatable to a higher pressure, but these characteristics could impede folding or wrapping the element tightly enough to fit through the cannula of a narrow-diameter pedicle opening. For these reasons, balloon elements for bone dilatation procedures would typically have thicker walls compared, for example, to the balloon elements commonly used for angioplasty procedures, but the bone dilatation balloons would generally be fabricated from more flexible, elastic materials than those used in angioplasty procedures.

Even if a balloon element can be wrapped or folded sufficiently tightly for insertion through the cannula of a narrow-diameter pedicle hole, it can later be difficult to remove or withdraw that balloon element through the same cannula following a dilatation procedure because, after a cycle of inflation and deflation inside a vertebral cavity, a balloon element may not be able to be refolded or rewrapped in-situ to its previously folded size or to a size sufficiently small to be withdrawn through the cannula without the use of excessive force which might crack or break the pedicle or tear the balloon from the catheter.

These problems were addressed, at least in part, by U.S. Pat. No. 7,488,337 (Saab et al.), which is incorporated herein in its entirety by reference. Saab '337 describes techniques for tensioning, stretching, folding and/or wrapping the expandable elements of devices designed for bone dilatation procedures to better facilitate insertion of the expandable elements into and, after an inflation procedure, withdrawal of the expandable elements from a bone structure through a narrow diameter cannula.

As noted above, however, the trend in medical practice in this field has been to utilize the smallest possible diameter hole or holes through the exterior portion of the bone to access the bone interior region. Current practice is to use an 11-gauge needle in order to perform a vertebral treatment, if possible, using bone openings that are so small (about 0.120 inches) that they can only accommodate an eleven (11) gauge cannula. Currently available catheter/expandable element apparatus for such bone treatment procedures, however, cannot be inserted into or withdrawn from a bone dilatation site through a standard wall 11-gauge cannula (which typically has an inside diameter of only 0.094 inches±0.002 inches). By contrast with an 11-gauge cannula, a thin-walled 10-gauge needle cannula (having a thinner wall thickness than a "standard" 10G cannula), which has become the industry standard for Kyphoplasty procedures, has an inside diameter of 0.114 inches (2.89 mm) The thin-walled 10-gauge cannula and its 0.114 inch inside diameter can accommodate current catheter assemblies used in these procedures, but it also has a larger outside diameter of about 0.134 inches that cannot fit inside a bone opening of only about 0.121 inches, which is the size of the opening made with an 11-gauge needle.

But, adapting the technology in this field to a smaller 11-gauge cannula, having an inside diameter (ID) of about 0.094 inches (2.39 mm)±0.002 inches and an outside diameter (OD) of about 0.120 inches (3.05 mm)±0.001 inches involves many substantial technological challenges. Much more is involved in this adaptation than just slightly shrinking all of the standard apparatus components.

First, because the volume of the bone interior that needs expanding remains unchanged, the expandable element must still be capable of expanding to that necessary bone interior volume, but that expandable element also needs to fit through the smaller interior diameter of an 11-gauge cannula. One approach to facilitate the insertion and removal steps with the larger, conventional 8-gauge and 10-gauge cannulas is to provide a slippery, friction-reducing coating or lubricating fluid (such as a silicone material) along the interior of the cannula, on the exterior of the expandable element, or both, to reduce friction and facilitate sliding the expandable element through the cannula.

A potential problem with this lubricant coating approach, however, is that at least a portion of such a lubricant would be transferred via the expandable element into the interior of the bone, where it would remain as a foreign contaminant. The presence of such a contaminant might cause irritation or an adverse body reaction at the interior bone site. In addition, the presence of a lubricating substance coating the walls of the expanded cavity of the bone following a dilatation procedure can possibly prevent a subsequently injected cement material from solidly and effectively bonding to the bone interior.

It also is not currently feasible to facilitate the use of an 11-gauge cannula in these procedures by reducing the wall thickness of the expandable element. As discussed above, the expandable element needs to withstand inflation to relatively high pressure without being punctured by irregularities or projecting portions of the bone interior. Furthermore, current medical protocols for bone dilatation procedures using an expandable balloon prescribe the minimum acceptable wall thickness for the expandable element, and those protocols must be met whether the balloon element needs to fit through the interior of a conventional 8-gauge or 10-gauge cannula, or through a very narrow diameter 11-gauge cannula.

Structural integrity and materials issues for the cannula create another significant design constraint. A "standard" 11-gauge cannula has an interior diameter (ID) of 0.094 inches with a tolerance of ±0.002 inches (i.e., an interior diameter that may range from 0.092 to 0.096 inches) and an outer diameter (OD) ranging from 0.119 to 0.121 inches (about 3.05 mm) In theory, one could make an ultra-thin walled 11-gauge cannula with an interior diameter of about 0.114 inches (i.e., comparable to a thin-walled 10-gauge cannula) but with a very thin wall such that the outer diameter was only about 0.120 inches. But, such an ultra-thin wall of only about 0.003 inches would compromise the structural integrity of the cannula which must function under demanding operating conditions. Such a modification would therefore raise numerous patient safety issues.

Another performance issue in this field is being able to accurately monitor the location of the expandable element as it is slid through the cannula and into the interior region of the bone that is being treated. This is an important issue because the length (along the catheter axis) of the expandable element (before inflation) is carefully selected to correspond to the size of the bone interior when the element is fully inflated.

Because of these narrow tolerances, it is important that the expandable element be properly situated in the bone interior before an inflation procedure is initiated. If the expandable element is pushed too hard and too far into the bone interior region, the distal tip of the catheter/expandable element may damage or even rupture the distal wall of the bone interior region. On the other hand, if the proximal portion of the expandable element is still located inside the cannula when the inflation procedure is started, the expandable element will be unable to fully inflate and, thus, unable to fully dilate the bone interior.

One approach to addressing the expandable element positioning problem has been to place radiopaque markings at one or more locations inside the expandable element and, using appropriate fluoroscopy equipment, to monitor the location of the expandable element by means of those markings as it is slid through the cannula and into the interior of the bone structure. Although the thickness of such radiopaque markings is generally very small, even that small added thickness becomes a significant factor in the context of wrapping or folding a full-sized bone dilatation expandable element to fit through the very small inside diameter of an 11-gauge cannula.

Yet another factor that becomes significant in the context of fitting a full-sized bone dilatation expandable element through the interior of an 11-gauge cannula is the juncture where the proximal end of the expandable element is secured to the distal end of the catheter shaft on which the expandable element is carried. Typically, the opening at the proximal end of the expandable element is formed slightly larger than the exterior diameter of the distal end of the catheter shaft. Thus, the proximal end of the expandable element can be slid over the distal end of the catheter shaft, and the expandable element can then be sealed to the end of the shaft by gluing, thermal bonding, or using similar sealing techniques. The result of this bonding procedure, however, is typically a small section of enlarged diameter at the juncture between the two components, and such an enlarged diameter section of the combined apparatus can inhibit passage of the expandable element through the interior of an 11-gauge cannula.

Still another design constraint of conventional expandable element bone dilatation systems is the use of a catheter shaft having an annular configuration with concentric inner and outer lumens. This coaxial, dual-lumen structure permits the outer lumen to be used for flowing a fluid (such as air, water or contrast fluid) to or from the expandable element for inflating or deflating the element once it is in place inside the bone, while using the separate inner lumen (which extends to the interior distal end of the expandable element) to contain a mandrel, rod or similar component. The mandrel may be moveable and slidable axially along the axis of the catheter assembly and may extend the length of the inner lumen into and to the distal end of the inner lumen and the expandable element.

At the same time, however, the separate, concentric lumen structure of such a catheter shaft takes up additional space and requires a larger diameter catheter shaft to achieve a given degree of cross-sectional area for fluid flow to/from the expandable element. In addition, this design generally increases the size of the wrapped or folded expandable element because in these configurations the inner catheter lumen typically extends through the interior of the expandable element.

These and other deficiencies in and limitations of the above-described prior art approaches to treating bone deformities, such as vertebral body compression fractures, and other medical treatments involving inserting and inflating an expandable element through a narrow cannula are overcome in whole or in part with the systems, apparatus and methods of this invention.

Specific Invention Background—Standard IBT Devices and Procedures and their Limitations As discussed above, surgical intervention at damaged or compromised bone sites has proven highly beneficial for patients, for example patients with back pain associated with vertebral damage.

Bones of the human skeletal system include mineralized tissue that can be generally categorized into two morphological groups: "cortical" bone and "cancellous" bone. Outer walls of all bones are composed of cortical bone, which has a dense, compact bone structure characterized by a microscopic porosity. Cancellous or "trabecular" bone forms the interior structure of bones. Cancellous bone is composed of a lattice of interconnected slender rods and plates known by the term "trabeculae."

During certain bone-related procedures, cancellous bone is supplemented by an injection of a palliative (or curative) material employed to stabilize the trabeculae. For example, superior and inferior vertebrae in the spine can be beneficially stabilized by the injection of an appropriate, curable material (e.g., PMMA or other bone cement or bone curable material). In other procedures, percutaneous injection of stabilization material into vertebral compression fractures, by, for example, transpedicular or parapedicular approaches, has proven beneficial in relieving pain and stabilizing damaged bone sites. Such techniques are commonly referred to in this art as vertebroplasty. Other skeletal bones (e.g., the femur) can be treated in a similar fashion. Bone in general, and cancellous bone in particular, can be strengthened and stabilized by palliative insertion or injection of bone-compatible material.

Using vertebroplasty as a non-limiting example, a conventional technique for delivering the bone stabilizing material entails placing a cannula using an internal stylet into the targeted delivery site. The cannula and stylet are used in conjunction to pierce the cutaneous layers of a patient above the hard tissue to be supplemented, then to penetrate the hard cortical bone of the vertebra, and finally to traverse into the softer cancellous bone underlying the cortical bone. Once positioned in the cancellous bone, the stylet is then removed, leaving the cannula in the appropriate position for delivery of curable material to the trabecular space of the vertebra that in turn reinforces and solidifies the target site.

In some instances, an effectiveness of the procedure can be enhanced by forming a cavity or void within the cancellous bone, and then depositing the curable material in the cavity. The cavity can be formed in various manners (e.g., mechanical cutting or shearing of cancellous tissue, expansion of a balloon or other expandable device to compress cancellous bone and also cause a "height" of the bone to increase, etc.). To minimize the duration of the procedure and number of tools required, it is desirable to use the same cannula to first guide delivery of the cavity-forming device and subsequently to deliver the curable material. One such procedure entails initially locating a distal end of the access cannula immediately adjacent the target site. The cavity-forming device is then delivered through the cannula to the target site and operated to form the cavity. The cavity will have an enlarged width (e.g., diameter) as compared to a diameter of the cannula. The cavity-forming device is then removed from the cannula, and curable material can be delivered to the target site via the cannula.

To get the curable material to fill the cavity, the surgeon can either inject the curable material through the cannula and any intervening space (between the distal end of the cannula and the cavity) to reach the cavity or else push the cannula through the intervening space until the distal end is suitably located in the cavity before delivering the curable material. Under the first approach, curable material is deposited into the intervening space and may undesirably solidify or attach to the cannula. Further, the intervening space represents an uncontrolled volume that may negatively affect the surgeon's evaluation of whether a necessary volume has been delivered to the cavity. With the second approach, it may be difficult for the surgeon to accurately re-position the cannula within the cavity and/or may cause unintended damage to the tissue surrounding the cavity and/or to the cannula.

The access cannula is normally a metal tube rigidly defining a central axis. Conventional cavity forming devices typically include a longitudinally linear shaft carrying the expandable body. With this linear configuration, the shaft/expandable body progresses from the access cannula into the bone structure along a relatively straight or linear path that is coaxial with the access cannula's central axis. This linear configuration, however, may inhibit the surgeon's ability to form the cavity at a desired location. For example, with Kyphoplasty the confined nature of the inner vertebral body and surrounding anatomy may necessitate insertion of the access cannula immediately adjacent to one of the vertebra's pedicles. This access site, in combination with the linear configuration of the access cannula and the shaft carrying the expandable body, dictates that the expandable body can only be located in a relatively limited area in line with the access cannula's central axis. In some instances, this restricted spatial positioning of the expandable body relative to the desired target site may not be optimal.

The standard design of an Inflatable Balloon Tamp (IBT) device (presently available from many sources) used for vertebral bone dilatation/treatment procedures consists of an inflatable, relatively thick-walled, elastomeric balloon connected to the outer lumen of a concentric lumen catheter shaft which, in turn, is connected to a bifurcation assembly at the proximal end of the device. The bifurcation assembly consists of two arms, one of which arms connects to the outer concentric lumen of the catheter shaft and is used for supplying an inflation fluid to the balloon, while the other arm is axially aligned with the catheter shaft and connects to the inner lumen of the catheter shaft of the device. This conventional arrangement allows access to the balloon's interior through the outer lumen to allow inflation and deflation of the balloon, and it also allows access to the balloon interior through the inner lumen of the catheter shaft. The inner lumen of the catheter shaft generally holds a 0.035 inch diameter stainless steel mandrel. The mandrel typically can be positioned so as to extend for the length of the interior of the inner lumen, but it can also be fully removed from the inner catheter lumen at the proximal end of the device. The mandrel also typically has a male luer bonded on its proximal end to allow a secure connection of the mandrel assembly to the luer lock on the straight arm of the bifurcation fitting. Radiopaque marker bands are located inside the balloon along the exterior of the inner shaft and are used to mark the proximal and distal ends of the balloon to assist the physician in positioning the balloon under fluoroscopy prior to inflation of the balloon.

The conventional IBT device is delivered to the vertebral body of a patient by means of a needle cannula. The standard for use in such procedures was originally a standard wall 8-gauge (0.135 inch or 3.4 mm inside diameter) needle together with a suitably sized IBT instrument. A smaller, thin-walled 10-gauge (0.114 inch or 2.89 mm inside diameter) needle was later introduced and has since gained favor because of its smaller size, which makes a smaller opening in the patient, and which in turn creates less trauma and aids in a quicker recovery time for the patient. The smaller size opening created with the 10-gauge needle also reduces the chances of fracture of the pedicle and provides the ability to treat smaller vertebrae that might not be able to accommodate an 8-gauge needle. In the bone dilatation form of a vertebral treatment procedure that uses an expandable element, an IBT device sized to accommodate the inner diameter of the cannula is introduced into the interior of the vertebral body of a patient. The expandable element of the device is then inflated inside the fractured vertebra. For a compression fracture, the procedure is intended to substantially restore the bone to its pre-fractured dimensions and, on withdrawal of the balloon, the space created by the inflated balloon can be filled with bone cement that hardens in place to stabilize the fracture.

A second, alternative form of a vertebral treatment procedure (one that is generally known in this art as "vertebroplasty"), however, can be performed without the use of an IBT device and without an expandable element. This alternative "vertebroplasty" procedure presently uses a standard eleven (11) gauge (0.094 inch or 2.4 mm inside diameter) needle cannula. But, rather than using an IBT device to first create a cavity to restore the vertebrae dimensions, in this alternative procedure the cement is injected directly into the vertebral body to stabilize the fracture. The medical decision about which of the two procedures should be performed in a particular case is best decided after the physician has fluoroscopically assessed the condition of the patient's vertebra.

The ability of a physician to decide between the two procedures at or shortly after the start of a procedure is currently limited, however, by the size of the opening into the bone interior. If the opening was created using an 11-gauge needle in anticipation of performing a vertebroplasty (no balloon element) procedure, that opening will not accommodate a cannula that is large enough to pass a conventional 10-gauge IBT assembly if the physician decides instead on the bone dilatation procedure. Accordingly, it would be highly desirable to have an IBT catheter assembly (including a conforming expandable element meeting current medical protocols) that is capable of fitting through the smaller interior opening of an 11-gauge needle cannula. This would allow the physician to start a procedure with a smaller entry opening in the skin and bone, use an 11-gauge cannula, and then still be able to select either type of bone treatment procedure, depending on which procedure is deemed best suited to the patient's condition. The ability to use an 11-gauge cannula in such procedures also would substantially reduce the chance of fracturing the pedicle (because a much reduced area of the pedicle would need to be opened to accommodate the smaller cannula), and it would also allow for the treatment of smaller vertebra as described above.

Accordingly, there is a currently unfilled need in this art for a system, apparatus and method wherein a narrow gauge (e.g., an 11-gauge) cannula can be utilized in combination with a specially designed catheter/expandable element apparatus adapted and sized to slide through the interior of the associated narrow gauge (e.g., an 11-gauge) cannula.

OBJECTS OF THE INVENTION

Accordingly, a general object of the present invention is to provide improved apparatus and methods for using a narrow gauge cannula for a bone dilatation and/or treatment procedure carried out with an inflatable balloon element.

Another general object of the present invention is to provide a combined system for a bone dilatation and treatment procedure, the system comprising a narrow gauge cannula sized to fit in a subcutaneous channel formed using an 11-gauge or smaller needle, in combination with a catheter shaft and expandable element assembly designed and sized for insertion into a bone/body location through the associated cannula.

Another general object of the present invention is to provide systems, apparatus and methods that enable a physician to utilize an 11-gauge or smaller cannula, positioned in a body/bone opening formed using an 11-gauge needle, to perform either a vertebroplasty procedure (with no balloon element) or, alternatively, a bone dilatation and/or treatment procedure using an expandable element positioned in the bone interior, using the same 11-gauge or smaller cannula depending on the physician's choice according to an assessment of the patient's condition.

A specific object of the present invention is to provide a catheter shaft and expandable element assembly (using a medically conforming expandable element according to current medical protocols), the assembly being designed and sized to fit through the interior of an 11-gauge cannula.

A specific object of the present invention is to provide a catheter shaft and expandable element assembly (using a medically conforming expandable element), wherein the expandable element (when properly folded or wrapped), the adjacent portion of the catheter shaft, and the juncture between the catheter shaft and the expandable element are adapted and sized: (1) to pass through the interior of an 11-gauge cannula to position the expandable element in the interior of a bone structure to be treated; and then, (2) following the steps of inflating, subsequently deflating, and re-wrapping/re-folding the expandable element, to also withdraw the expandable element through the interior of the same 11-gauge cannula.

Another specific object of the present invention is to provide a catheter shaft and expandable element assembly (using a medically conforming expandable element) designed and sized to fit through the interior of an 11-gauge cannula in the absence of any lubricant or other friction-reducing coating.

Another specific object of the present invention is to provide a catheter shaft and expandable element assembly (using a medically conforming expandable element) designed and sized to fit through the interior of an 11-gauge cannula with radiopaque markings at the distal tip of the expandable element but at no other location along the expandable element.

Another specific object of the present invention is to provide a catheter shaft and expandable element assembly (using a medically conforming expandable element) designed and sized to fit through the interior of an 11-gauge cannula with at least a radiopaque marking at or near the proximal end of the interior of the expandable element, with or without a radiopaque marking at or near the distal end of the interior of the expandable element, and with or without another such marking at or near the distal tip.

Still another specific object of the present invention is to provide a catheter shaft and expandable element assembly (using a medically conforming expandable element) designed and sized to fit through the interior of an 11-gauge cannula in which the outside diameter of the assembly at the juncture between the catheter shaft and the expandable element is substantially the same as the outside diameter of the distal end of the catheter shaft.

Yet another specific object of the present invention is to provide a catheter shaft and expandable element assembly (using a medically conforming expandable element) designed and sized to fit through the interior of an 11-gauge cannula in which the interior of the catheter shaft comprises a single lumen.

Another specific object of the present invention is to provide a catheter shaft and expandable element assembly (using a medically conforming expandable element) designed and sized to fit through the interior of an 11-gauge cannula in which the assembly comprises a "floating" mandrel capable of limited axial movement along or parallel to the catheter axis in a direction toward or away from the distal end of the assembly by bonding the distal end of the mandrel and providing an enclosed channel or sleeve of limited length in which the unbonded proximal end of the mandrel can slide.

Still another specific object of the present invention is to provide a catheter shaft and expandable element assembly (using a medically conforming expandable element) designed and sized to fit through the interior of an 11-gauge cannula in which the assembly comprises a mandrel with a distal end bonded at the distal end of the assembly and with an unbounded, axial moveable proximal end that may, in some cases, extend externally of the proximal end of the catheter shaft.

Still another specific object of the present invention is to provide a catheter shaft and expandable element assembly (using a medically conforming expandable element) designed and sized to fit through the interior of an 11-gauge cannula in which the assembly additionally comprises one or more features in accordance with U.S. Pat. No. 7,488,337 for actively or passively tensioning, stretching, folding and/or wrapping the expandable element, especially to facilitate removal of the expandable element through a narrow gauge cannula following an inflation/bone dilatation and/or treatment procedure.

It is also an object of the present invention to provide a medical device system comprising in combination a narrow gauge cannula (as defined hereinafter) and a catheter shaft/expandable element assembly (using a medically conforming expandable element) wherein the catheter/expandable element assembly is designed and sized to fit through the interior of the narrow gauge cannula both prior to and subsequent to an inflation procedure.

It is a specific object of this invention to provide a medical device system comprising in combination an 11-gauge cannula (as defined hereinafter) and a catheter shaft/expandable element assembly (using a medically conforming expandable element) wherein the catheter/expandable element assembly is designed and sized to fit through the interior of the 11-gauge cannula both prior to and subsequent to an inflation procedure.

Yet another object of the present invention is to provide a catheter shaft and expandable element assembly including a mandrel.

Another object of the present invention is to provide a catheter shaft and expandable element assembly including a mandrel wherein the mandrel is bonded at its distal end to the expandable element.

Another object of the present invention is to provide a catheter shaft and expandable element assembly including a mandrel wherein the mandrel is bonded at its distal end to the expandable element using a spring element to improve the bonding between the distal end of the mandrel and the distal end of the expandable element.

Another object of the present invention is to provide a catheter shaft and expandable element assembly including a mandrel wherein the mandrel is bonded at its distal end to the expandable element wherein the distal end of the mandrel and the distal portion of the assembly are configured to facilitate active or passive deflection of the distal tip portion of the mandrel or core wire and of the distal end of the assembly.

Another object of the present invention is to provide a catheter shaft and expandable element assembly including a mandrel wherein the mandrel is bonded at its distal end to the expandable element wherein the distal end of the mandrel and the distal portion of the assembly are configured to facilitate active or passive deflection of the distal tip portion of the mandrel or core wire and of the distal end of the assembly and further wherein the proximal end of the catheter assembly is configured to apply axial force when desired to the proximal end of the mandrel to cause active deflection of the distal tip.

Still another object of the present invention is to provide a catheter shaft and expandable element assembly including a mandrel wherein a distal portion of the mandrel or core wire and the distal portion of the assembly are configured to improve the flexibility of the distal end of the assembly to facilitate better navigating curves or bends during placement of the expandable element at a desired treatment site.

Other objects and advantages of the present invention will in part be obvious and will in part appear hereinafter. The invention accordingly comprises, but is not limited to, the apparatus and related methods, involving the several steps and the various components, and the relation and order of one or more such steps and components with respect to each of the others, as exemplified by the following description and the accompanying drawings. Various modifications of and variations on the apparatus and methods as herein described will be apparent to those skilled in the art, and all such modifications and variations are considered to be within the scope of the invention.

SUMMARY OF THE INVENTION

The following definitions will apply to terms of art as used in this application:

The term "11-gauge needle" as used in this application refers to a needle that creates an opening about 0.120 inches in diameter, preferably ranging from 0.119 to 0.121 inches, in diameter.

The term "narrow gauge cannula" as used in this application broadly refers to a cannula having an outside diameter that is less than the diameter of an opening made by a 10-gauge needle, in other words less than about 0.134 inches. For purposes of this application, a cannula that fits into the opening made by an 11-gauge needle or smaller, namely an opening with a diameter of about 0.121 inches or less, is regarded as a "narrow gauge cannula."

The term "11-gauge cannula" as used in this application refers to a cannula or a needle cannula having an outside diameter of about 0.120 inches, preferably plus or minus 0.001 inches (i.e., ranging from 0.119 to 0.121 inches).

The term "standard 11-gauge cannula" as used in this application refers to a cannula or a needle cannula having an outside diameter of about 0.120 inches, preferably plus or minus 0.001 inches (i.e., ranging from 0.119 to 0.121 inches), and having an open interior diameter of about 0.094 inches, preferably plus or minus 0.002 inches (i.e., ranging from 0.092 to 0.096 inches).

The term "medically conforming catheter" or "medically conforming catheter shaft" or "conforming catheter shaft" as used in this application refers to a catheter that satisfies current (2012) medical protocols for performing this type of bone dilatation or treatment procedure.

The term "medically conforming expandable element" or "conforming balloon" as used in this application refers to a balloon element having at least a wall thickness that satisfies current (2012) medical protocols for performing this type of bone dilatation or treatment procedure.

The present invention provides systems, apparatus and methods for treating and stabilizing bone structures by accessing and dilating such bone structures using an 11-gauge cannula and thereafter filling the interior of the bone structure with a bone-compatible cement or similar material. The present invention provides a catheter shaft and expandable element assembly (using a wrapped or folded expandable element that meets current medical protocols in this field, especially with regard to minimum wall thickness) that can be slid through the interior of an 11-gauge or smaller cannula before and after a dilatation or treatment procedure.

The present invention also provides a medical device system comprising a catheter assembly in accordance with this invention in combination with an 11-gauge cannula that has been specially prepared to adapt it for use with the catheter assembly of this invention by not applying any friction-reducing coatings to the interior of the cannula or to any exterior portion of the catheter shaft or expandable element. Additionally, the present invention also comprises methods for fabricating and configuring the catheter assembly and the cannula of this invention and methods for utilizing the several component elements that comprise this invention in conjunction with one another.

The distal end of the catheter assembly of this invention will enter and exit the interior of an 11-gauge needle cannula without any added lubrication, which is unique compared with other similar products currently available. As described below, this functionality is accomplished by a number of novel design and fabrication innovations. Among the novel design and fabrication innovations of some embodiments of this invention are the elimination of the inner catheter shaft and the modification of moving the radiopaque markings from inside the balloon, where they can interfere with and enlarge the wrapped profile of the balloon and thus compromise its ability to pass through the cannula easily, to the distal end of the device. As discussed hereinafter, however, in other invention embodiments it has been found possible to place one or two very thin radiopaque bands under the balloon and still wrap or fold it tightly enough to fit through the interior of an 11-gauge cannula.

In still another invention embodiment, eliminating the inner shaft and fixing the distal tip of a novel "floating" mandrel provides a configuration having the needed axial stiffness to properly place the device in a vertebral body while also allowing movement of the elastomeric polymer structures during balloon inflation without placing undue stress on the distal balloon bond. This invention embodiment also allows the balloon to stretch in length instead of bunching up during a removal step following an inflation/bone treatment procedure, and in this way this design feature further facilitates withdrawal of the deflated balloon through the interior of an 11-gauge cannula.

More particularly, the catheter/expandable element assembly of the present invention is specially designed and adapted to fit through an eleven (11) gauge cannula or needle cannula (both for insertion and for removal following an inflation/treatment procedure) while still providing an expandable element having a suitable balloon wall thickness (i.e., a 0.010 inch double wall thickness (DWT) or greater) to resist puncture by bone fragments during an inflation/bone dilatation and/or treatment procedure and to meet existing medical protocols. The several novel and unique cooperating synergistic design adaptations of this invention that make it possible to fabricate a catheter/expandable element assembly that can be slid through the interior of an 11-gauge cannula (for insertion or for removal following an inflation procedure) are described in greater detail below.

A first design change that characterizes the present invention is the substitution of a single lumen catheter shaft for the dual concentric lumen configuration found on conventional IBT devices.

A second design change that characterizes the present invention is the replacement of the conventional fully removable mandrel (which is ordinarily located in the inner catheter lumen of the concentric, dual-lumen catheter shaft) with a redesigned mandrel and a novel structure at the proximal end of the assembly. The redesigned mandrel of the present invention is not removable, but rather is a relatively permanent, integral part of the catheter/expandable element assembly. In the mandrel design of the present invention, the mandrel is capable of only limited, constrained axial movement (along or parallel to the axis of the catheter assembly) toward or away from the distal end of the assembly, and the extent of such movement is defined by a sleeve or channel at the proximal end of the assembly in which the free proximal end of the mandrel can slide.

These design modifications eliminate a large volume of material from the distal structure of the device, which in turn allows the balloon to be wrapped or folded into a smaller diameter (i.e., a reduced-diameter wrapped balloon profile), which in turn facilitates passage of the assembly through a smaller diameter needle cannula. In addition, the present invention incorporates a unique and completely novel "floating mandrel" design in which the mandrel is attached at the distal balloon bond but is nevertheless able to slide parallel to the long axis of the catheter shaft because the mandrel is not bonded at the proximal end of the device. This novel configuration allows the polymer body of the catheter assembly to shrink slightly during the pre-use sterilization and storage steps without causing severe distortion of the device. Such distortion could occur over time if both the proximal and distal ends of the mandrel were fixed at the respective ends of the device.

Providing for constrained axial movement of the mandrel also allows the elastomeric portion (expandable element) of the device to expand in length during an inflation procedure to very high pressures while the mandrel exerts little or no force on the distal balloon bond because the mandrel is allowed to move axially with the expanding elastomeric portion of the device as it grows in length during inflation. By contrast, if the mandrel were fixed at both ends within the device, the stretching of the balloon and outer shaft during an inflation procedure could result in peeling away the distal end of the elastomeric element from its bond to the mandrel and causing detachment of the mandrel from the distal bond.

If the mandrel were to detach and the balloon were to fail, the mandrel could then puncture the balloon and exit the device into the bone interior through the failed section of the balloon.

To maintain the mandrel inside the catheter assembly at the proximal end of the assembly, while permitting constrained axial movement, a ball or other enlarged geometric feature is provided at the proximal end of the mandrel such that the ball or geometric feature can be captured by a suitable mandrel retaining structure provided within the bifurcation assembly portion located at the proximal end of the device. This ball or enlarged proximal end of the mandrel is captured at the proximal end of the device where the mandrel passes through a male fitting which has a hole drilled in its luer stem, such hole being smaller in diameter than the size of the ball or other enlarged geometric feature, thereby preventing the geometric feature (and the proximal end of the mandrel) from passing through the luer lock. The proximal end of the mandrel is thus able to slide within a sleeve portion of the proximal assembly end, but that axial movement is limited, for example to about 8 mm, of longitudinal (axial) motion.

At its distal end, the mandrel is preferably embedded in the balloon bond at the distal tip of the balloon to prevent the mandrel from exiting the interior of the balloon if the balloon should fail. In a preferred invention embodiment, this is achieved by using a stainless steel, helically coiled mandrel bonding spring element, typically about 2 mm in length, attached to the distal end of the mandrel. The mandrel bonding spring element preferably comprises a coil of stainless steel wire at least about 0.007 inches in diameter for structural integrity. Approximately 1 mm of the approximately 2 mm long spring element extends from the distal end of the mandrel. This 1 mm length of spring section extending from the distal end of the mandrel is encapsulated with a suitable material, such as a high durometer (e.g., 75D) polyurethane polymer which fills the spring's interior and covers the exterior of its most distal 1 mm length of coils in polyurethane.

The use of high durometer polyurethane provides a strong anchor for the balloon bond to the mandrel bonding spring coil interior so that this bond will resist deformation and failure during inflation of the balloon. This polyurethane encapsulation is then also preferably bonded to the interior of the distal balloon neck. With the distal end of the mandrel bonding spring thus encapsulated, the distal tip of the mandrel stays within the balloon bond even if the balloon should split through the distal neck of the balloon during a balloon failure.

In another preferred embodiment design feature of this invention, a radiopaque distal tip may also be incorporated into the polyurethane encapsulation at the distal tip of the device. The radiopaque marker used in the distal tip of an 11-gauge IBT catheter assembly in accordance with an embodiment of this invention can be formed using the following multi-step process. The first step is mixing a tungsten filler, which is made into a fine powder, with a suitable polymer. Polyurethane is a preferred polymer for this application. The polymer is blended and pelletized in preparation for the next fabrication step. The second step is an extrusion process. In this step, the pellets are fed into an extruder where they are melted and formed into a solid radiopaque marker rod (beading) typically about 1 mm in diameter. The last step is to cut the radiopaque marker rod into small lengths, e.g., 2 to 3 mm long, and those short lengths are bonded inside the distal balloon neck portion of the expandable element by thermal or adhesive means. Once the length of radiopaque marker rod is bonded, the distal tip is trimmed to a suitable length leaving about 1 mm of radiopaque marker rod in the distal tip of the catheter assembly.

Alternatively, the spring element itself used to secure the distal end of the mandrel could be fashioned from a radiopaque metal (e.g., platinum) or from an alloy of a radiopaque metal, which could be easily viewed under fluoroscopy. It would be necessary, however, for the radiopaque metal or alloy used for this mandrel bonding spring fabrication to have the necessary tensile strength sufficient for reliable operation in this capacity.

The design of the proximal and distal ends of the mandrel can be varied and still function effectively substantially as described herein. In alternative invention embodiments, the distal end of the mandrel could be in the form of braided wires, a hypotube with holes or slots, slots or holes made in the distal end of the mandrel, or other means of establishing the passages where a material, such as a polymer, can be flowed or otherwise applied during assembly to fill in open spaces and to form a strong mechanical bond to the distal end of the mandrel when the polymer hardens. In still other embodiments, a distal portion of the mandrel may comprise a reduced diameter section, or a spring section, or a flattened section to provide increased flexibility of the mandrel, at least for a mandrel portion located inside the expandable element. In some embodiments, the distal end of the mandrel may comprise a core wire with a hooked or angled end that can engage a distal portion of a spring element located inside the expandable element to provide active deflection of the distal tip of the expandable element.

In other alternative invention embodiments, the proximal ball end of the mandrel could be substituted by a hooked or angled proximal mandrel end, for example with the end folded over on itself, or by any other means to make it larger in diameter such that the proximal mandrel end is retained by a male cap or other mandrel proximal end retaining structure to provide comparable retention functionality to the ball proximal end design. In other alternative invention embodiments, proximal end of mandrel may extend beyond the proximal end of the catheter shaft and be axially moveable to apply tensioning to the distal end.

In still another important aspect of this invention, the bond juncture (where the expandable element and the catheter shaft are joined and sealed) is formed such that the maximum diameter of the catheter assembly at this juncture is less than the smallest possible inside diameter of a standard 11-gauge cannula (i.e., 0.092 inches based on an ID of 0.094 inches with a tolerance off 0.002 inches). This sizing allows the passage of the catheter assembly through the 11-gauge cannula without the need for any lubricating fluids. Currently available catheter assemblies for these bone dilatation applications employ a lap joint as a means to attach the proximal balloon neck of the expandable element to the catheter shaft. This means that the balloon proximal neck must be placed over the distal end of the catheter shaft prior to bonding these components, and this approach requires that the balloon neck ID must be greater than the shaft outside diameter at this juncture. This type of construction (i.e., balloon neck over the shaft) creates a juncture that would typically be slightly smaller than the original outer diameter of the balloon neck prior to bonding if a thermal bonding procedure is used (because there is some melting that occurs with the thermal bonding). Alternatively, the juncture would be about the same diameter as the outer diameter of the balloon neck if an adhesive bonding procedure is used. In either of these cases, however, the juncture between the catheter shaft and the balloon neck for the balloon-neck-over-the-catheter-shaft configuration would necessarily be significantly larger than the outside diameter of the distal end of the catheter shaft because of the added thickness of the balloon neck.

By contrast, the catheter assembly of this invention preferably utilizes a butt-joint bonding procedure in which the distal end of the catheter shaft is butt up against the proximal balloon neck (which can be substantially the same outer diameter as the catheter shaft), and the two components are bonded by an adhesive bonding, solvent bonding, thermal bonding or equivalent bonding procedure. In this fabrication procedure, the juncture between the catheter shaft and the balloon neck can have substantially the same diameter as the catheter shaft and the balloon neck. The resulting bond is very close or identical in diameter to the original catheter shaft diameter. This fabrication approach, which is novel in this field, reduces the maximum outer diameter of the catheter assembly at this critical juncture location by as much as 25% compared with conventional catheter assemblies being used for this procedure.

Additionally, as discussed above, catheters currently available employ lubricating fluids to a great extent, coating these devices quite heavily in order to facilitate sliding a catheter that has a marginal interference fit with the inside diameter of the cannula through the interior of the cannula and without damage to the catheter assembly. Without the heavy use of such lubrication, these conventional catheter assemblies would be unable to pass through the cannula or would do so only with force and great difficulty. However, these lubricating fluids are generally silicone-based oils which can cause contamination of the interior bone site and also interfere with adhesion when they are transferred to the interior of a bone structure that is being treated. These lubricating fluids can be carried by the expandable element and transferred to the interior of the vertebra, thereby compromising the adhesion of cement to the bone in a subsequent treatment step. The advantages of employing the butt-joined shaft/balloon bond as described above, in combination with one or more of the other novel design and fabrication innovations of this invention, make it possible to completely eliminate the use of lubricating fluids which can contaminate the interior of the vertebral cavity, cause interference with complete adhesion of cement to the bone, and also expose the patient's bone interior to these substances.

In addition, in other embodiments, the design and fabrication features of this invention as herein described may be used in combination with the features taught by U.S. Pat. No. 7,488,337 for tensioning, stretching, folding and/or wrapping the expandable element, especially to facilitate removal of the expandable element through an 11-gauge cannula following an inflation/bone dilatation procedure.

The following are particularly preferred embodiments of the present invention:

1. A catheter/expandable element assembly for medical applications comprising a conforming catheter shaft having proximal and distal ends, an expandable element having an expandable balloon portion bonded at the distal end of the catheter shaft, and a fluid passageway extending from a proximal end of the catheter shaft to the interior of the balloon portion of the expandable element, the assembly being characterized by one or more of the following features:

(a) the expandable element comprises a conforming balloon which can be folded or wrapped to a maximum diameter of less than 0.092 inches;

(b) the assembly including both a wrapped/folded balloon portion and a juncture between the catheter shaft and a proximal balloon neck portion will fit through the interior of a standard 11-gauge medical cannula;

(c) the assembly including both a wrapped/folded balloon portion and a juncture between the catheter shaft and a proximal balloon neck portion will fit through the interior of a standard 11-gauge medical cannula without the use of any lubricant or similar friction-reducing substance;

(d) the expandable element can be folded or wrapped to sufficiently reduce the cross-sectional profile of the assembly to be compatible with the use of a narrow gauge cannula;

(e) the expandable element can be folded or wrapped to sufficiently reduce the cross-sectional profile of the assembly to be compatible with the use of an 11-gauge or smaller-diameter cannula;

(f) the catheter shaft is a single lumen catheter shaft and the assembly including both a wrapped/folded balloon portion and a juncture between the catheter shaft and a proximal balloon neck portion fits through the interior of a standard 11-gauge medical cannula;

(g) the expandable element comprises a proximal neck portion that is butt-jointed by an adhesive bonding procedure, a solvent bonding procedure or a thermal bonding procedure to the distal end of the catheter shaft;

(h) the expandable element comprises a distal neck portion having a sealed tip, and the sealed tip contains the only radiopaque marker along the expandable element;

(i) the expandable element comprises one or more bands of a radiopaque material under a balloon portion of the element with or without radiopaque material at a distal tip of the expandable element;

(j) the assembly additionally comprises a mandrel element that extends from a proximal end of the assembly, through the catheter shaft, and through the expandable element to an interior distal end of the assembly;

(k) the assembly additionally comprises a mandrel element that extends from an interior proximal end of the assembly, through the catheter shaft, and through the expandable element to an interior distal end of the assembly and further wherein a distal end of the mandrel is bonded to the interior distal end of the assembly;

(l) the assembly additionally comprises a catheter bifurcation assembly at the proximal end of the catheter shaft;

(m) the assembly additionally comprises a catheter bifurcation assembly at a proximal end having an inflation arm portion and a mandrel arm portion, where the mandrel arm portion is substantially in axial alignment with the catheter shaft;

(n) the assembly additionally comprises a catheter bifurcation assembly at a proximal end having an inflation arm portion and a mandrel arm portion, where the mandrel arm portion is substantially in axial alignment with the catheter shaft and further wherein the proximal end of the mandrel arm portion provides an enclosed sleeve for limited axial movement of the mandrel and the proximal end of the mandrel is of an enlarged size such that the proximal end of the mandrel is retained in the sleeve;

(o) the assembly additionally comprises a mandrel element and a balloon-wrapping and/or tensioning device for actively or passively applying axial and/or rotational forces to the balloon portion following a balloon inflation and treatment procedure and subsequent deflation but prior to the withdrawal step causing the balloon portion to stretch axially and/or to wrap at least in part around a mandrel element to reduce the profile of the balloon portion and thereby facilitate the withdrawal step;

(p) the assembly additionally comprises a mandrel element that extends from an interior proximal end of the assembly, through the catheter shaft, and through the expandable element to an interior distal end of the assembly, and further wherein a distal end of the mandrel is bonded to the distal end of the assembly and an unbonded proximal end of the mandrel has an enlarged geometrical feature that can move axially along or parallel to the axis of the catheter shaft but only within an enclosed sleeve that is bounded at its proximal end by the interior proximal end of the assembly and is bounded at its distal end by a mandrel retaining structure;

(q) the assembly additionally comprises a mandrel element that extends from a proximal end of the assembly, through the catheter shaft, and through the expandable element to an interior distal end of the assembly, wherein a distal portion of the mandrel is of a reduced diameter relative to a more proximal portion of the mandrel;

(r) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion;

(s) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion, and additionally comprising an elongated spring element with spring coils that surround the mandrel beginning at a location proximal of the expandable element and extending into and through the expandable element to a distal tip of the expandable element where the distal end of the spring is bonded, and furthermore wherein the hooked mandrel tip engages one or more of the spring coils;

(t) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion, and additionally comprising an elongated spring element with spring coils that surround the mandrel beginning at a location proximal of the expandable element and extending into and through the expandable element to a distal tip of the expandable element where the distal end of the spring is bonded, and furthermore wherein the hooked mandrel tip engages one or more of the spring coils, and also wherein there is greater spacing between adjacent spring coils along a distal portion of the spring than along a more proximal spring portion;

(u) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion, and additionally comprising an elongated spring element with spring coils that surround the mandrel beginning at a location proximal of the expandable element and extending into and through the expandable element to a distal tip of the expandable element where the distal end of the spring is bonded, and furthermore wherein the hooked mandrel tip engages one or more of the spring coils, and also wherein the spring is covered by a polymeric sleeve;

(v) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion, and additionally comprising an elongated spring element with spring coils that surround the mandrel beginning at a location proximal of the expandable element and extending into and through the expandable element to a distal tip of the expandable element where the distal end of the spring is bonded, and furthermore wherein the hooked mandrel tip engages one or more of the spring coils, and also wherein the proximal end of the mandrel extends proximally of the assembly and terminates in an enlarged geometrical feature whereby the mandrel can be axially tensioned by pulling on that proximal mandrel end so as to compress the spring where the hooked mandrel tip engages the spring coils and thereby causing the distal end of the expandable element to temporarily deflect from an axial orientation for as long as the mandrel is axially tensioned; and, (w) the assembly additionally comprises a mandrel element that extends from a proximal end of the assembly, through the catheter shaft, and into the expandable element, wherein at least the portion of the mandrel inside the expandable element tapers to a flattened distal end that terminates in an unbonded angled or hooked mandrel tip at a location proximate to the distal end of the balloon portion, and additionally comprising an elongated spring element with spring coils that surround the mandrel beginning at a location proximal of the expandable element and extending into and through the expandable element to a distal tip of the expandable element where the distal end of the spring is bonded, and furthermore wherein the hooked mandrel tip engages one or more of the spring coils, and also comprising a mandrel tensioning assembly consisting of two threadably-engaged mandrel tensioning elements at the proximal end of the catheter/expandable element assembly whereby the threadably-engaged tensioning elements provide an axial channel in which the proximal end of the mandrel can slide such that rotating one tensioning element relative to the other causes one of the tensioning elements to move in a proximal direction relative to the second element thereby applying axial tensioning to the mandrel and causing deflection of the hooked mandrel tip and the distal tip of the expandable element as long as the axial tensioning is applied.

2. A system for carrying out a medical dilatation and/or a cavity creation, enlargement or treatment procedure at an internal body site comprising a catheter/expandable element assembly according to any combination of characterizing features of the invention as described in paragraph 1 above, in combination with an 11-gauge cannula capable of delivering the expandable element from outside the body to the desired internal body site.

3. A system for carrying out a medical dilatation and/or a cavity creation, enlargement or treatment procedure at an internal body site comprising a catheter/expandable element assembly according to any combination of characterizing features of the invention as described in paragraph 1 above, in combination with a narrow gauge cannula capable of delivering the expandable element from outside the body to the desired internal body site.

4. A system according to either of paragraphs 2 or 3 above, wherein the interior of the cannula is free of any lubricant and also wherein no lubricant is applied to the catheter/expandable element assembly.

5. A method for carrying out a medical treatment that includes a dilatation and/or a cavity creation, enlargement or treatment procedure using a catheter/expandable element assembly according to any combination of characterizing features of the invention as described in paragraph 1 above, the method comprising the steps of: (a) inserting at least the expandable element portion of the assembly through an 11-gauge cannula to position the expandable element in the interior of a bone or body site; (b) inflating the expandable element inside the interior of the bone or body site to a size and/or inflation pressure and for a time sufficient to complete the treatment; (c) deflating the expandable element; and (d) withdrawing the expandable element portion of the assembly through the cannula.

6. A method for carrying out a medical treatment that includes a dilatation and/or a cavity creation, enlargement or treatment procedure using a catheter/expandable element assembly according to any combination of characterizing features of the invention as described in paragraph 1 above, the method comprising the steps of (a) inserting at least the expandable element portion of the assembly through a narrow gauge cannula to position the expandable element in the interior of a bone or body site; (b) inflating the expandable element inside the interior of the bone or body site to a size and/or inflation pressure and for a time sufficient to complete the treatment; (c) deflating the expandable element; and, (d) withdrawing the expandable element portion of the assembly through the cannula.

7. A method according to either of paragraphs 5 or 6 above, additionally comprising a step of stretching, folding and/or wrapping the expandable element following step (c) and prior to step (d).

8. A method for carrying out a medical treatment that includes a dilatation and/or a cavity creation, enlargement or treatment procedure using a system according to either of paragraphs 2 or 3 above, the method comprising the steps of: (a) positioning the cannula in a body location so that a distal end of the cannula is proximate to the intended treatment site; (b) inserting at least the expandable element portion of the assembly through the cannula to position the expandable element in the interior of a bone or body site without the use of any lubricants; (c) inflating the expandable element inside the interior of the bone or body site to a size and/or inflation pressure and for a time sufficient to complete the treatment; (d) deflating the expandable element; and, (e) withdrawing the expandable element portion of the assembly through the cannula without the use of any lubricants.

9. A method of manufacturing the assembly of the invention as described in paragraph 1 above, by bonding the catheter shaft to the expandable element, the method comprising the steps of butting an end of the catheter shaft against a similarly-sized open end of the expandable element followed by an adhesive bonding procedure, a solvent bonding procedure or a thermal bonding procedure for securing the two abutting ends to one another thereby creating a fluid passageway through the interior of the catheter shaft and into the balloon portion of the expandable element.

10. A method of manufacturing the assembly of the invention as described in paragraph 1 above, including positioning a mandrel inside the assembly for restricted axial movement of the mandrel, the method comprising the steps of bonding the distal end of the mandrel to the inside distal end of the expandable element and positioning the proximal end of the mandrel inside an enclosed sleeve at the proximal end of the assembly.

11. The method of manufacturing the assembly of the invention as described in paragraph 10 above, wherein the mandrel has an enlarged proximal end that cannot pass through an aperture in a mandrel retention structure at the proximal end of the catheter/expandable element assembly that thereby retains the enlarged proximal end of the mandrel in the sleeve.

12. A method of practicing the invention according to either of paragraphs 5 or 6 above, additionally comprising a step, between steps (a) and (c), of temporarily deflecting the distal tip of the expandable element out of axial alignment by applying axial tensioning to the slidable proximal end of a mandrel having a hooked mandrel distal tip that engages at least some of the coils of a coiled spring element surrounding the mandrel inside the expandable element, where the distal end of the spring element is bonded to the distal tip of the expandable element.

13. A method of practicing the invention according to paragraph 12 above, further comprising a step, before step (d), of relaxing the axial tensioning of the mandrel and allowing the expandable element to return to axial alignment by action of the spring element.

14. A method of practicing the invention according to either of paragraphs 5 or 6 above, additionally comprising a step, between steps (a) and (c), of rotating one of two threadably engaged mandrel tensioning elements at a proximal end of the assembly in a first rotation direction so as to move the rotating element in a proximal direction thereby axially tensioning the mandrel of the assembly, which engages at its distal end a spring element located inside and fixed to the end of the expandable element, causing deflection of the tip of the expandable element out of axial alignment.

15. A method of practicing the invention according to paragraph 1 above, further comprising a step, before step (d), of rotating the rotatable threaded tensioning element in a second rotation direction so as to relax the axial tensioning of the mandrel and to permit the spring element to return the expandable element to axial alignment.

These and other variations and embodiments of the systems and apparatus of this invention, and different applications for and methods of fabricating and using such apparatus, will be apparent from the accompanying drawings and the following descriptions of the drawings.

DETAILED DESCRIPTION OF PREFERRED EMBODIMENTS

FIGS. 1A to 1E illustrate various aspects of a first embodiment of a catheter/expandable element assembly 10 according to this invention. The assembly of FIGS. 1A to 1E is specially designed and adapted, as explained below, to fit through the interior of a very narrow gauge (e.g., an 11-gauge) medical cannula without the use or presence of any lubricants.

Figure 1A:
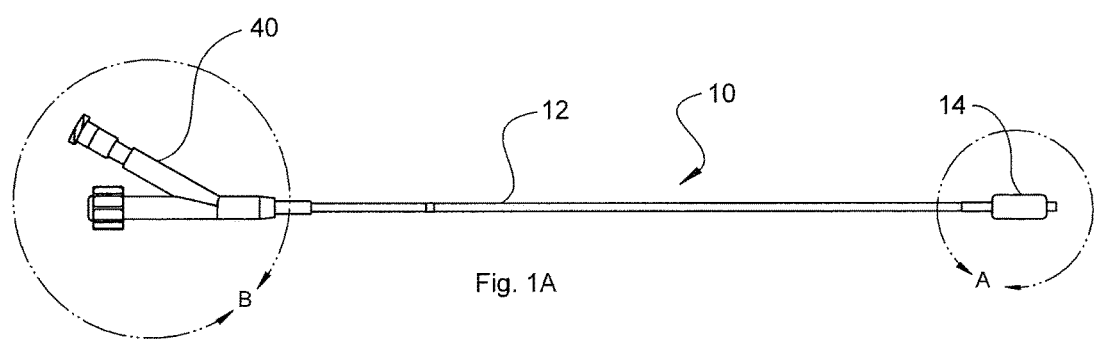
FIG. 1A (sheet 1/14) is a schematic elevational view of a catheter/expandable element apparatus according to an embodiment of the invention.

The assembly 10 of FIG. 1A comprises a single lumen catheter shaft 12 of suitable dimensions typically fabricated from a thermoplastic material using conventional fabrication techniques, as are well-known in this art. The catheter shaft 12 would be of a suitable length (or would be trimmed to a suitable length) to extend from a location outside a human body to the site of a bone or other body part to be treated. The catheter shaft 12 would ordinarily have a generally uniform wall thickness of suitable dimensions to insure structural integrity, while leaving the maximum possible open cross-sectional interior region to accommodate a mandrel element (as described hereinafter) and for flowing an inflation fluid to and from the expandable element that is bonded to the distal end of the catheter shaft. Catheter shaft 12 is a "conforming" catheter shaft, which is defined herein as a shaft fabricated to meet all existing relevant medical standards in this field.

At the same time, the outer diameter (O.D.) of catheter shaft 12 must be approximately equal to or preferably at least slightly smaller than the inside diameter (I.D.) of the narrow gauge cannula through which apparatus 10 needs to pass. For a standard 11-gauge (11G) cannula, the I.D. is 0.094 inches with a tolerance of ±0.002 inches, meaning that the O.D. of catheter 12 should not be greater than 0.092 inches for use in an 11G system. In a specific embodiment of the present invention, for example, the outer diameter of the catheter shaft is 0.080 inches, the outer diameter of the proximal neck portion of the expandable element is about 0.085 inches (so that the outer diameter at the butt-joined juncture between the distal end of the catheter shaft and the proximal neck portion of the expandable element is also about 0.085 inches), and the diameter of the conforming balloon (when folded) is about 0.087 to 0.089 inches. Thus, this assembly according to this invention would pass through the interior of a standard 11G cannula (with a minimum inside diameter of 0.092 inches) even without the use of any lubricant. No existing catheter assembly for these applications has or can achieve these small diameter sizes.

FIG. 1A additionally shows a conforming expandable element 14 (shown in an inflated state) at the distal end of the assembly 10 and a bifurcation apparatus 40 at the proximal end of the assembly 10. These features are described in greater detail below with reference to FIGS. 1B, 1C, 1D and 1E.

Figure 1B:
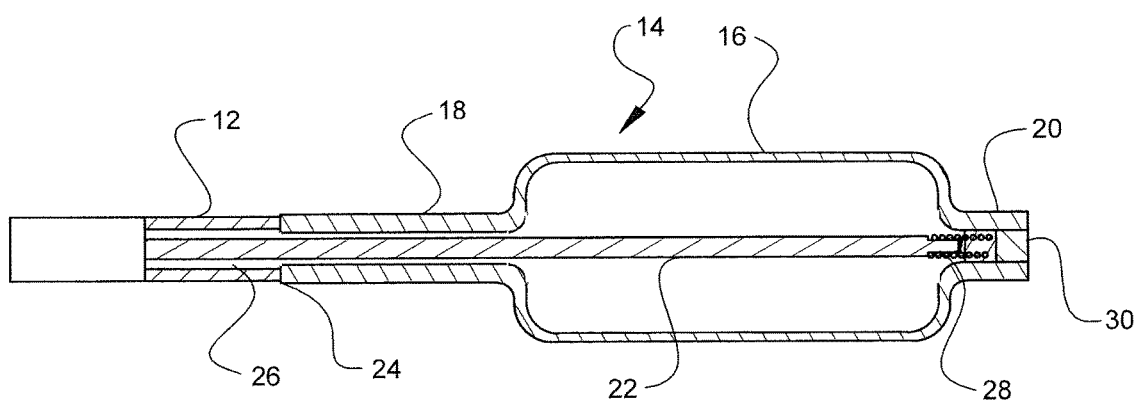
FIG. 1B (sheet 2/14) is an exploded, schematic sectional view of the distal end (i.e., that portion inside the circle A) of the apparatus illustrated in FIG. 1A.

FIG. 1B is an exploded sectional view of the expandable element 14 (in an inflated state) at the distal end of the assembly 10 in FIG. 1A. As seen in FIG. 1B, expandable element 14 comprises an inflatable balloon portion 16 having a proximal balloon neck portion 18 and a distal balloon neck portion 20. A mandrel 22 extends from the proximal end of assembly 10 (FIG. 1A), through the catheter shaft 12, and through expandable element 14 to the interior distal end of the distal balloon neck portion 20. In a preferred invention embodiment, the distal end of mandrel 22 is bonded to the interior distal end of the distal balloon neck portion 20.

The inflatable balloon portion 16 of expandable element 14 is a conforming full-sized balloon made of a suitable elastomeric material according to current medical protocols in this field, and the balloon 16 has a wall thickness and design that also satisfies all current medical protocols in this field. For purposes of this invention, such balloons will be referred to herein as "conforming balloons." Although the balloon 16 as seen in FIGS. 1A and 1B is shown in an inflated state for illustration purposes, it will be understood by those skilled in this art that the balloon 16 would be deflated and folded or wrapped to realize a smaller cross-sectional profile for insertion into and withdrawal from a bone or body treatment site through a cannula.

In a preferred invention embodiment, the proximal neck portion 18 of the expandable element 14 is "butt-jointed" to the distal end of the catheter shaft 12 at a juncture location 24 with a suitable adhesive, or by solvent bonding, or by thermal bonding or any other bonding procedure. As discussed earlier, this is a structural and fabrication innovation that in part distinguishes the catheter/expandable element assembly of this invention from prior art apparatus intended for similar applications. As a result of this butt-jointed bond between the catheter shaft 12 and proximal neck 18 of expandable element 14, the outer diameter of assembly 10 at juncture 24 is substantially identical to the O.D. of catheter shaft 12 at its distal end, which is also substantially identical to the O.D. of proximal neck portion 18 of expandable element 14. This structure facilitates maximizing the O.D. and I.D. of catheter shaft 12, which is advantageous, while maintaining the minimum possible cross-sectional profile at every location (including at juncture 24) along assembly 10 that needs to fit through the interior of, for example, an 11G or other narrow gauge cannula.

As seen in FIG. 1B, the I.D. of catheter shaft 12 at juncture 24, the I.D. of proximal neck portion 18 at juncture 24, and the O.D. of mandrel 22 need to be sized such that a fluid connection 26 exists between the interior of catheter shaft 12 and the interior of expandable element 14 at juncture 24 so that an inflation fluid can be introduced to, and subsequently removed from, balloon 16 when the balloon is properly positioned in the bone or body location that is being treated.

In alternative invention embodiments, the mandrel 22 may or may not be bonded at its distal end to the expandable element 14. In one embodiment, the distal end of mandrel 22 can be directly bonded with a suitable adhesive or bonding material to the inside of distal neck portion 20 of element 14. As shown in FIGS. 1B and 1E, however, in a preferred invention embodiment a mandrel bonding spring element 28 of a suitable size is bonded at a spring proximal end to the distal end of mandrel 22 and the distal end of the spring is bonded to neck portion 20. The mandrel bonding spring element is one preferred approach to more securely bonding the distal end of mandrel 22 to the inside of distal neck portion 20 of expandable element 14.

In this embodiment, which is best seen in FIG. 1E, mandrel bonding spring element 28 may have spring coils of an inner diameter sized to fit around the distal end of mandrel 22. As better seen in FIG. 1E, mandrel 22 can be formed to have a reduced diameter at its distal end 23 so as to accommodate spring 28 while the outer diameter of the spring coils can be substantially the same as the outer diameter of the more proximal portion 25 of mandrel 22. Mandrel bonding spring element 28 can be positioned such that a proximal portion of spring 28 (e.g., a spring portion about 1 mm long) surrounds the distal end 23 of mandrel 22 and a distal portion of spring 28 (e.g., a spring portion about 1 mm long) extends beyond the end of mandrel 22 into the interior of neck portion 20 (FIG. 1B). The spring 28 can then be securely bonded (e.g., by an adhesive, by welding, by soldering, etc.) to both the end of mandrel 22 and to the interior of neck portion 20. For example, the spring 28 can be impregnated with 75D polyurethane on its interior and exterior to enable it to bond securely to the mandrel and the inside of neck portion 20. The impregnated polyurethane holds the mandrel's distal end in place in the balloon bond even if the distal balloon bond should fail and rupture.

As shown in the invention embodiment of FIG. 1B, there are no radiopaque markings inside balloon 16. This is another important distinction between some embodiments of the catheter/expandable element assembly of this invention and prior art apparatus. As discussed above, the conventional practice of placing one or more radiopaque markings inside balloon 16 has been found (in at least some instances) to impair the ability to wrap or fold a conforming balloon as tightly as needed to reduce its profile sufficiently to pass through the interior of an 11-gauge cannula. Instead, assembly 10 as seen in FIGS. 1A and 1B includes a radiopaque material at the sealed distal tip 30 of expandable element 14 for purposes of assisting a physician in properly positioning the balloon 16 at a treatment site. For example, the polyurethane seal that comprises distal tip 30 may contain a radiopaque material such as tungsten.

In some embodiments of this invention, however, it has been found possible to place one or two very thin radiopaque bands (e.g., a 0.003 inch thick platinum marker band) under the balloon and still wrap or fold it tightly enough to fit through a standard 11-gauge cannula. Thus, in alternative invention embodiments, radiopaque markings may be limited to the distal tip of the expandable element 14 as shown in FIG. 1B, or there may be a radiopaque band near the proximal end of the balloon portion 16 with or without a radiopaque element at the tip (not shown in the drawings), or there may be radiopaque bands under each of the proximal and distal ends of the balloon portion 16, again either with or without a radiopaque element at the tip (not shown in the drawings).

Figure 1C:
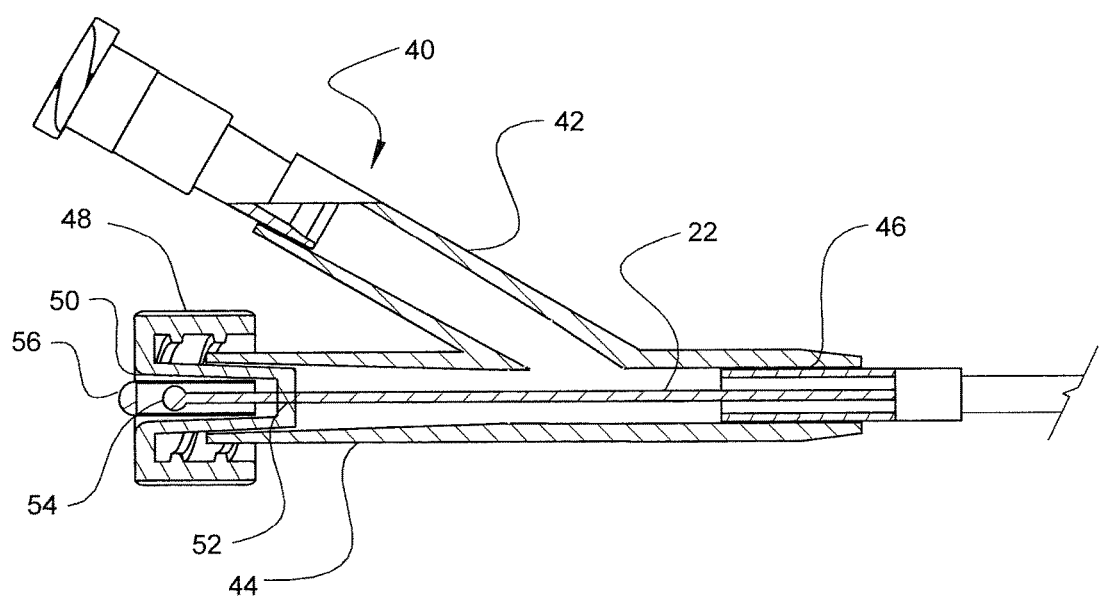
FIG. 1C (sheet 3/14) is an exploded, schematic sectional view of the proximal end (i.e., that portion inside the circle B) of an embodiment of the apparatus illustrated in FIG. 1A.
Figure 1D:
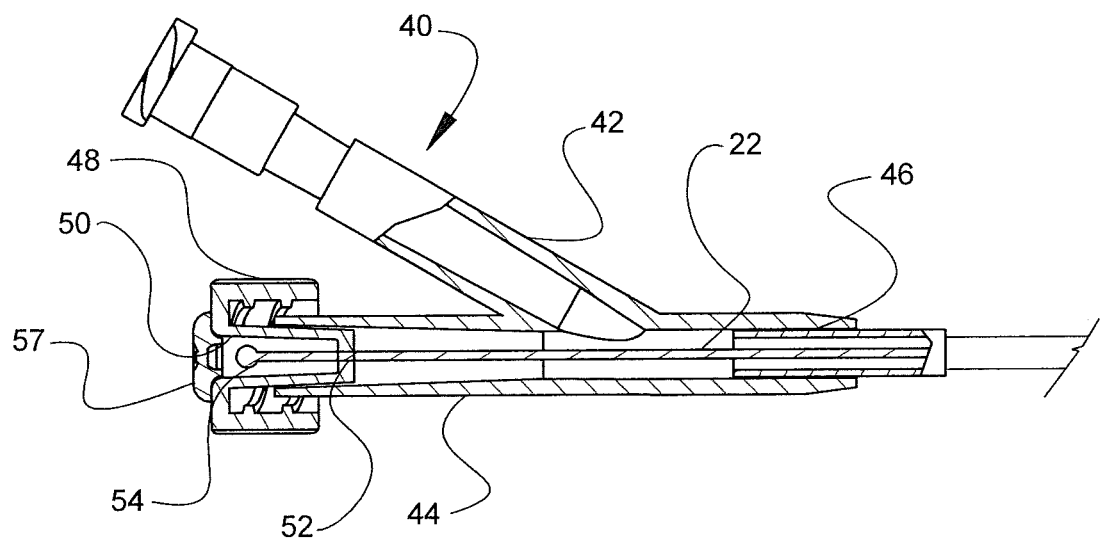
FIG. 1D (sheet 4/14) is an exploded, schematic sectional view of the proximal end (i.e., that portion inside the circle B) of an alternative embodiment of the apparatus illustrated in FIG. 1A.
Figure 1E:
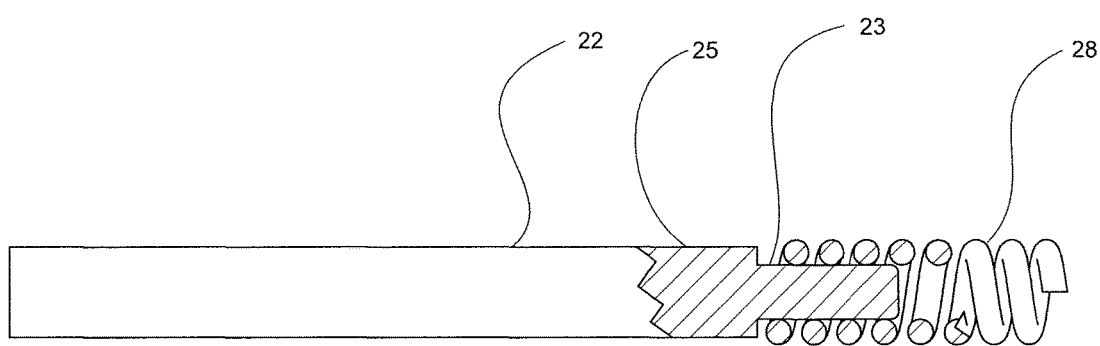
FIG. 1E (sheet 5/14) is another exploded, schematic partial sectional view of a portion of the distal end of the apparatus illustrated in FIG. 1A, specifically showing additional details of an invention embodiment wherein a spring element is bonded to a reduced-diameter distal end of the mandrel.

FIGS. 1C and 1D illustrate in greater detail the features of the proximal end of assembly 10 as seen in FIG. 1A. FIG. 1C shows a first form of a catheter bifurcation assembly 40 that is specially adapted for the preferred "floating" mandrel embodiment of the present invention. As seen in FIG. 1C, the catheter bifurcation assembly 40 consists of an inflation fluid side arm 42 and a mandrel retention arm 44 which is substantially in axial alignment with the catheter shaft. The catheter bifurcation assembly 40 is bonded or otherwise connected to the catheter shaft along juncture 46. The inflation fluid arm 42 functions in a conventional manner and is used to add or withdraw inflation fluid from the device for alternatively inflating or deflating the balloon.

The mandrel retention arm 44, however, is designed and operates differently than the second arm of conventional catheter bifurcation assemblies. In contrast to catheter assemblies where the mandrel is fully axially moveable along the catheter axis (toward or away from the distal end) and, in fact, can be completely withdrawn from the proximal end of the mandrel arm, mandrel 22 of the present invention is only capable of restricted axial movement and is maintained inside arm 44 and catheter shaft 12 during nominal operation of the device.

An embodiment of the "floating" mandrel feature of this invention is illustrated in FIG. 1C. The proximal end of mandrel retention arm 44 is sealed by means of a male cap 48 which may, for example, be internally threaded to mate with external threads at the proximal end of arm 44. Male cap 48 has a centrally-located recess portion 50 extending from the proximal end exterior of the cap into the interior of arm 44. At the distal end of recess 50, an aperture 52 sized to just accommodate mandrel 22 extends through the wall portion of male cap 48 at the distal end of recess 50 into the interior of arm 44. The open proximal end of recess 50 is sealed by suitable means, such as a plug 56, after the mandrel 22 has been inserted. The length of recess 50 will define the allowable axial movement of mandrel 22.

The proximal end of mandrel 22 comprises a geometric feature that is larger than aperture 52, for example a ball end 54, but which is smaller than the inside diameter of recess 50 such that the proximal end of mandrel 22 can slide in recess 50 but cannot slide through aperture 52. Thus, in this configuration of elements, recess 50 of male cap 48 forms a sleeve of a limited length in which mandrel 22 can slide without exiting from arm 44.

In a preferred design feature of this invention embodiment, as seen in FIG. 1C, the wall defining the interior of the proximal end of arm 44 has a slight inward taper in the distal direction, and, correspondingly, the wall defining the outside and the inside of recess 50 has a similar inward taper. This configuration facilitates obtaining a tight seal between the male cap 48 and the interior of arm 44 under the pressurized conditions that exist during a balloon inflation procedure. In another preferred design feature of this invention embodiment, as shown in FIG. 1C, the open proximal end of recess 50 is sealed (after inserting mandrel 22) by means of a dome-ended tubular sealing member or plug 56 sized to fit securely inside recess 50. Such a tubular sealing member 56 can be retained in place by compression fitting (utilizing the inward taper of recess 50), or by bonding, or by other suitable means.

FIG. 1D is generally comparable to FIG. 1C, except that FIG. 1D uses a modified design for the combination of cap 48/plug 56 of FIG. 1C. As seen in FIG. 1D, capping element 57 replaces plug 56. Capping element 57 does not extend into the recess 50. Capping element 57 may be formed separate from cap 48 and it may lock or screw into place or otherwise mate with cap 48.

Figure 2A:
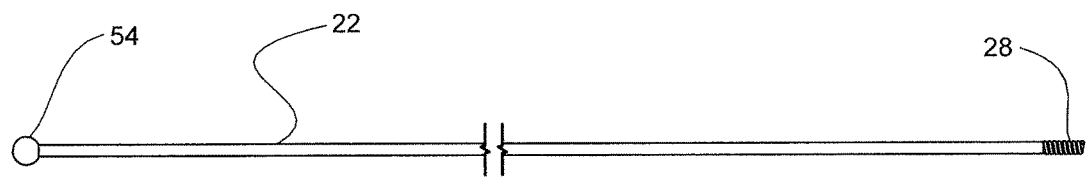
FIGS. 2A and 2B (sheet 6/14) are schematic elevational views of alternative embodiments of a mandrel according to the present invention showing alternative enlarged proximal end configurations.
Figure 2B:
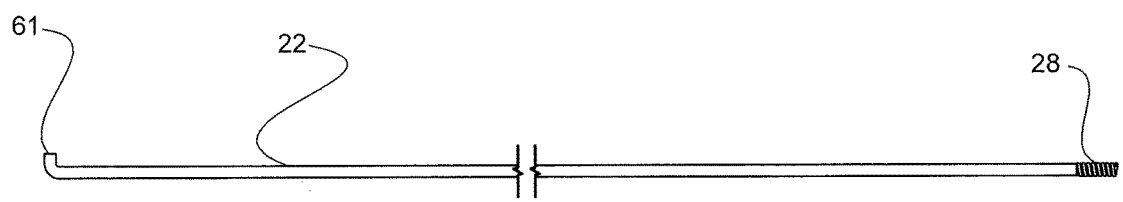

FIGS. 2A and 2B illustrate alternative invention embodiments of mandrel 22. As in the embodiment of FIGS. 1A to 1E, at its distal end mandrel 22 is bonded to a mandrel bonding spring element 28 to assist in more securely fixing the distal end of the mandrel to the distal neck 20 of expandable element 14 (FIG. 1B). In FIG. 2A, the proximal end of mandrel 22 is a ball-shaped feature 54 that is larger than the diameter of mandrel 22 (as seen in FIGS. 1C and 1D). In FIG. 2B however, in place of the ball element 54 of FIG. 2A, the geometric feature that prevents the proximal end of mandrel 22 from passing through aperture 52 (FIGS. 1C and 1D) is a hook-shaped end 61. Other types of geometric features could similarly be substituted for ball element 54 or hook element 61.

Figure 3:
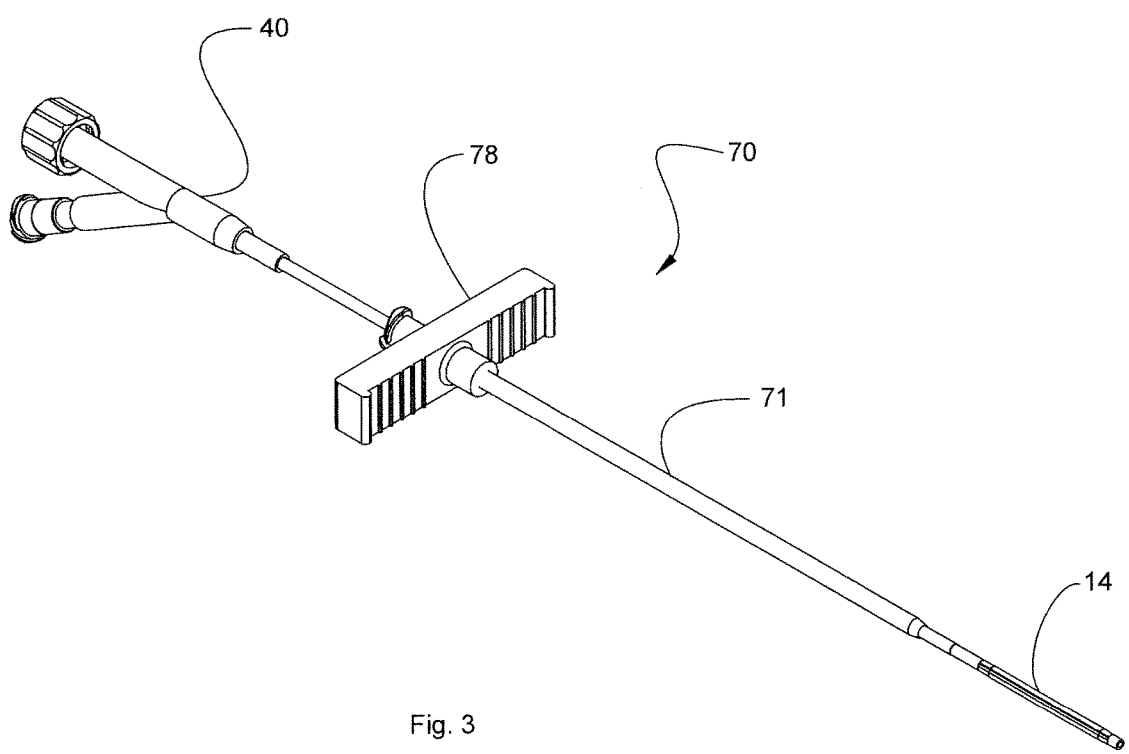
FIG. 3 (sheet 7/14) is a schematic isometric view of a medical device system comprising a narrow gauge (e.g., an 11-gauge) cannula in combination with a catheter/expandable element assembly, each of the components being specially adapted for use with one another in accordance with embodiments of this invention.
Figure 4:
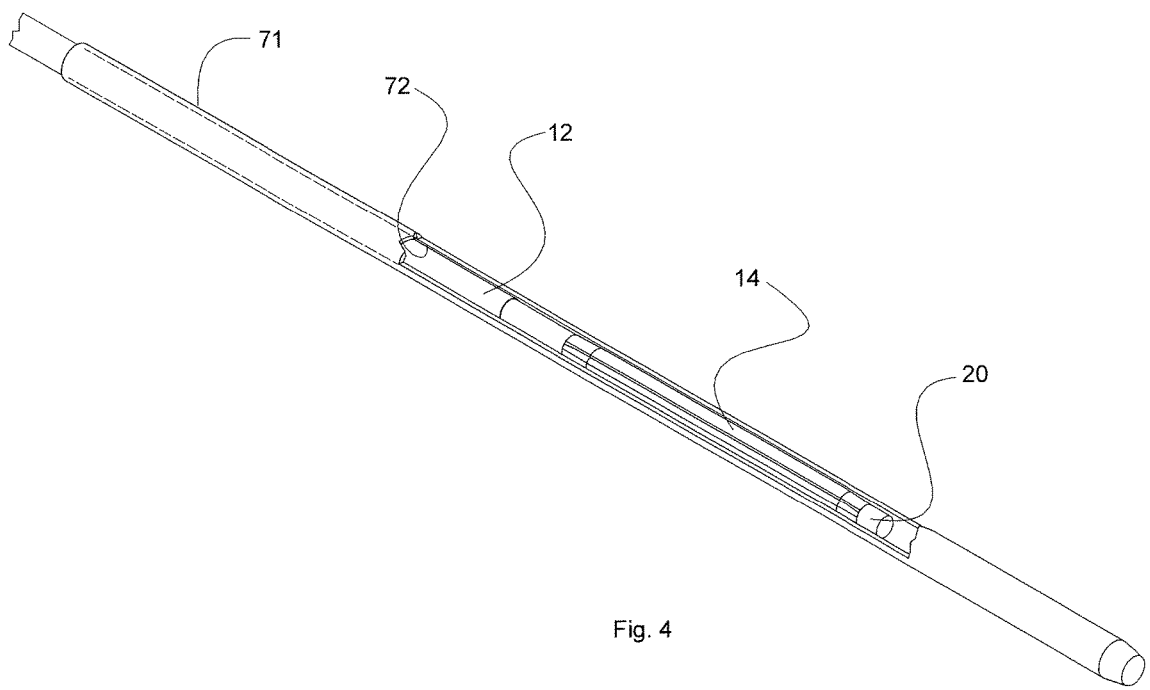
FIG. 4 (sheet 8/14) is a schematic, partially cutaway view illustrating the expandable element component of the medical device system of FIG. 3 located inside the narrow gauge cannula component of the system.

FIG. 3 illustrates a narrow gauge (e.g., an 11G) medical cannula system 70 suitable for use in the medical device systems of this invention. FIG. 3 shows a view in which the expandable element 14 (shown in a wrapped or folded state) of catheter assembly 10 has completely passed through the interior of cannula 71. FIG. 4 is an expanded, partially cutaway view of the cannula 71 as seen in FIG. 3 with an expandable element 14 (again shown in a wrapped or folded state) having a distal tip 20 and the associated catheter shaft 12 located inside cannula 71. System 70 includes narrow gauge cannula 71, which may be an 11-gauge cannula, having a standardized I.D. of 0.094 inches±0.002 inches in combination with catheter assembly 10, as previously described. System 70 may also advantageously include a handle element 78 to assist a physician in maneuvering the device. Cannula 71 has been specially adapted for use in this invention by not applying any lubricant to the interior wall 72 of cannula 71. Similarly, as seen in FIG. 4, no lubricant has been applied to the exterior of expandable element 14. As discussed above, the specialized design and fabrication features of this invention (which reduce the cross-sectional profile of the catheter/expandable element assemblies of this invention), enable the catheter shaft 12 and expandable element 14 of catheter assembly 10 to fit through the interior of cannula 71 without the use of any lubricants or similar substances.

Table 1 below presents comparative size data for three differently sized medical cannulas: a standard 8-gauge (8G) cannula; a thin-walled 10-gauge (10G) cannula; and a standard 11-gauge (11G) cannula. As previously discussed, the standard 8G and thin-walled 10G cannulas have been used for bone treatment procedures. Prior to the present invention, however, size constraints have essentially made it impossible to utilize 11G cannulas for the type of bone treatment procedures that require positioning an expandable element inside a bone structure. The data in Tables 1 and 2 below help to illustrate how size constraints have impeded use of standard 11G cannulas in this type of bone treatment procedure prior to the innovations of this invention.

TABLE 1

| Cannula Size Gauge # | Inner Diameter (ID) inches | Cross-sectional Area of cannula opening sq. inches | Outer Diameter (OD) inches | Cross-sectional Area of body aperture needed to accommodate the cannula sq. inches |
| --- | --- | --- | --- | --- |
| Standard 8G (Prior Art) | 0.135 | 0.014314 | 0.165 | 0.021383 |
| Thin-walled 10G (Prior Art) | 0.114 | 0.010207 | 0.134 | 0.014103 |
| 11G (Present Invention) | 0.094 | 0.006940 | 0.120 | 0.011310 |

For "standard" cannulas, the gauge number assures a standardized inner diameter (ID) within very narrow tolerances and a standardized wall thickness for required structural integrity. For example, for a standard 11G cannula, the ID is set at 0.094 inches±0.002 inches. This assures that the ID of a standard 11G cannula will fall between 0.092 and 0.096 inches. The corresponding OD for a standard gauge cannula is established by adding to the standardized ID the necessary cannula wall thickness required for structural integrity.

Table 1 illustrates for example that the cross-sectional area of the cannula opening for a standard 11G cannula is only about 68% as large as the cross-sectional area of the cannula opening for a thin-walled 10G cannula, which correspondingly requires a much smaller diameter catheter/expandable element assembly in order to fit through that smaller cannula opening. But, there is also a corresponding reduction in the outer diameter (OD) of the 11G cannula. Therefore, the 11G cannula can be placed in a much smaller-sized opening in a patient's skin and bone (e.g., in an opening made with an 11-gauge needle) that has a cross-sectional area that is 20% smaller than the cross-sectional area of the opening needed to accommodate the larger 10G cannula. This means that a 20% smaller hole (based on area) needs to be made in a patient's bone structure; 20% less bone/tissue needs to be removed or displaced (which means less patient trauma); and, there is a greatly reduced chance of fracturing a delicate bone structure like a vertebral segment.

Table 2 below presents comparative size data for the folded balloon elements associated with catheter/expandable element assemblies intended for use with three differently sized medical cannulas: a standard 8G cannula; a thin-walled 10G cannula; and a standard 11G cannula.

TABLE 2

| Folded Balloon Size for Corresponding Gauge # | Cross-sectional Area of Folded Balloon (sq. inches) | Cross-sectional Area of cannula opening (sq. inches) |
|---|---|---|
| Standard 8G (Prior Art) | 0.01458 | 0.014314 |
| Thin-walled 10G (Prior Art) | 0.008012 | 0.010207 |
| 11G (Present Invention) | 0.006225 (average of low of 0.005945 sq. in. and high of 0.006504 sq. in.) | 0.006940 (0.094 ID) 0.006648 (0.092 ID) |

Table 2 shows the measured cross-sectional areas of three folded balloon elements compared with the cross-sectional areas of the cannula openings for the associated cannulas. Each of the three balloon elements has the same wall thickness as mandated by existing medical protocols in this field. Table 2 illustrates that an 11G cannula has an opening that can clearly accommodate the folded balloon of an expandable element/catheter assembly according to this invention, but not the folded balloon of current 10G systems.

In particular, Table 2 shows that balloon elements fabricated according to the present invention can be folded to a size that is about 52% smaller in cross-sectional area than the comparable measurement for a balloon used for a conventional 8G device (i.e., the folded balloon elements of this invention will fit through a cannula interior having a cross-sectional area that is about 52% smaller than the balloons used for an 8G device). Table 2 further shows that balloon elements according to the present invention can be folded to a size that is about 22% smaller in cross-sectional area than the comparable measurement for a balloon used for a conventional 10G device (i.e., the folded balloon elements of this invention will fit through a cannula interior having a cross-sectional area that is about 22% smaller than the balloon used for a 10G device).

The criticality of these size differences becomes even more apparent when comparing the data of Tables 1 and 2. Neither of the 8G or the 10G folded balloons would be expected to fit through the interior of a standard 11G cannula because the cross-sectional areas of these folded balloons is greater than the cross-sectional area of the cannula opening for an 11G cannula. On the other hand, a folded balloon element and catheter assembly in accordance with this invention (having an average diameter of about 0.089 inches and a cross-sectional area of about 0.006225 sq. in.) would fit through the interior of an 11G cannula, even at the lower I.D. tolerance limit of 0.092 inches (a cannula opening of 0.006648 sq. in.).

Other advantageous embodiments of this invention will now be described with reference to FIGS. 5-8B. In some invention embodiments, it may be desirable to provide for added flexibility, or to provide for active deflectability, along the distal portion of the catheter/expandable element assembly, particularly the mandrel. The distal portion of the mandrel in this context refers to at least the portion of the mandrel that is located inside the expandable element of the catheter assembly. The distal portion of the mandrel as used in connection with the embodiments of FIGS. 5-8B may more broadly refer to a portion of the mandrel that begins inside the catheter shaft and extends through the proximal neck portion of the expandable element, through the balloon, to the distal neck portion of the expandable element. In some of these embodiments, a combination of a proximally located tube or rod element in conjunction with a distally located flexibility and/or deflection spring element are provided inside the catheter shaft to add the desired flexibility/deflectability functionality.

Figure 5:
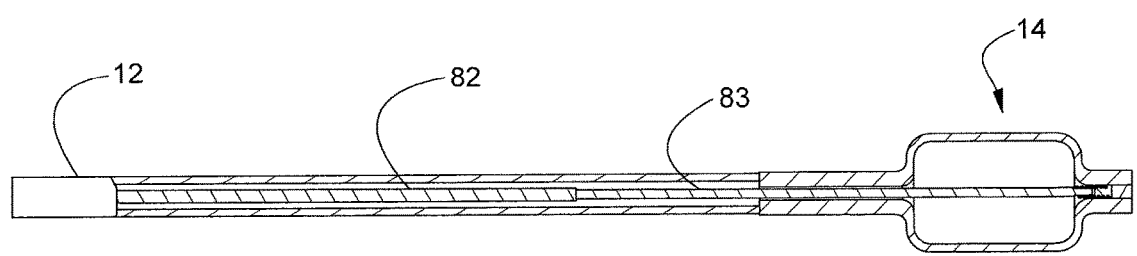
FIG. 5 (sheet 9/14) is an exploded, schematic sectional view of the distal end (i.e., that portion inside the circle A) of an assembly comparable to that illustrated in FIG. 1A showing an alternative invention embodiment for configuring the distal portion of the mandrel.

FIG. 5 illustrates a modified mandrel configuration that provides added flexibility at the distal end of the catheter/expandable element assembly. Expandable element 14 is shown in an inflated state. A proximal portion 82 of the mandrel is of normal size in FIG. 5, while a distal portion 83 of the mandrel, beginning inside catheter shaft 12 and extending through expandable element 14, is of a reduced diameter. The reduced diameter of mandrel section 83 provides additional flexibility that can facilitate maneuvering the expandable element 14. In other respects, however, the embodiment of FIG. 5 is comparable to that shown in FIG. 1B.

FIGS. 6A to 6D and 7A to 7C illustrate invention embodiments that provide for active deflection of the distal end of the mandrel and of the distal end of the expandable element to which the distal end of the mandrel is bonded. Such active deflection can provide additional maneuverability that can facilitate optimizing placement of the expandable element for a treatment procedure.

Figure 6A:
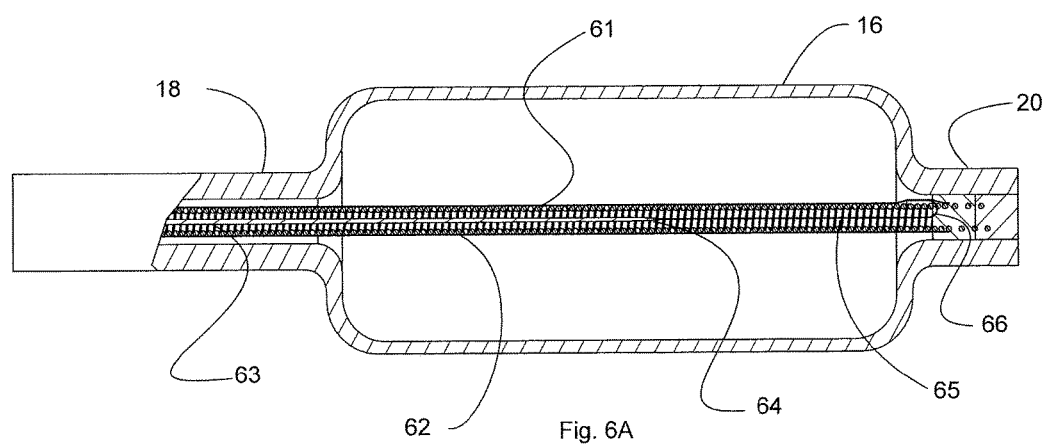
FIG. 6A (sheet 10/14) is an exploded, schematic sectional view of the distal end (i.e., that portion inside the circle A) of an assembly comparable to that illustrated in FIG. 1A showing an alternative invention embodiment for providing an actively deflectable mandrel/expandable element configuration.

FIG. 6A is an exploded, schematic sectional view of the distal end of a catheter/expandable element assembly showing a balloon element 16, a proximal neck portion 18 and a distal neck portion 20 (as in FIG. 1B). In FIG. 6A, however, the distal end of mandrel 63 tapers to a taper point 64, and the portion 65 of the mandrel that is distal of taper point 64 is flattened (as better seen in FIG. 7C), ending in a curved or hooked end 66. As also seen in FIG. 6A, at a distal end of the assembly, a deflectability spring 61 surrounds mandrel 63 (inside the catheter shaft) and extends into the distal tip of the assembly where it is bonded (comparable to the configuration seen in FIG. 1B). In this respect, deflectability spring 61 serves a function comparable to mandrel bonding spring 28 in FIG. 1B.

Figure 7A:
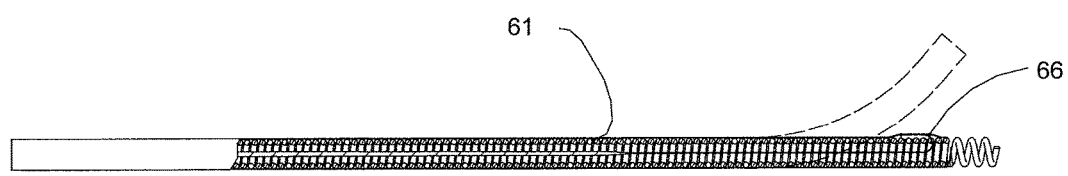
FIG. 7A (sheet 12/14) shows a schematic view of the distal end of the mandrel and spring element components of FIGS. 6A and 6C being actively deflected using a mandrel deflection mechanism as seen in FIG. 6B at the proximal end of the assembly.

As also seen in FIG. 6A, the hooked end 66 of mandrel 63 engages one or more coils of deflectability spring 61 near, but proximal of, the point where spring 61 is bonded to distal tip 20. Because of this feature, applying axial tensioning to the proximal end of mandrel 63 in a proximal direction results in actively deflecting the distal end of the mandrel (as seen in FIG. 7A) with the result of also deflecting the distal end of the expandable element.

Figure 6B:
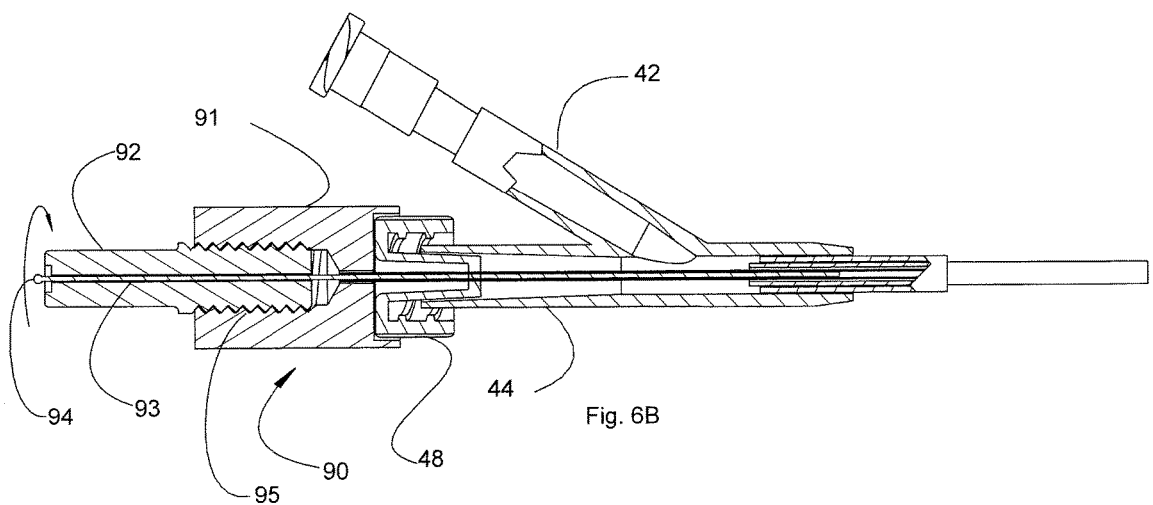
FIG. 6B (sheet 10/14) is an exploded, schematic sectional view of the proximal end (i.e., that portion inside the circle B) of an assembly comparable to that illustrated in FIG. 1A showing an alternative proximal end invention embodiment for providing the actively deflectable mandrel/expandable element configuration as seen in FIG. 6A.
Figure 6C:
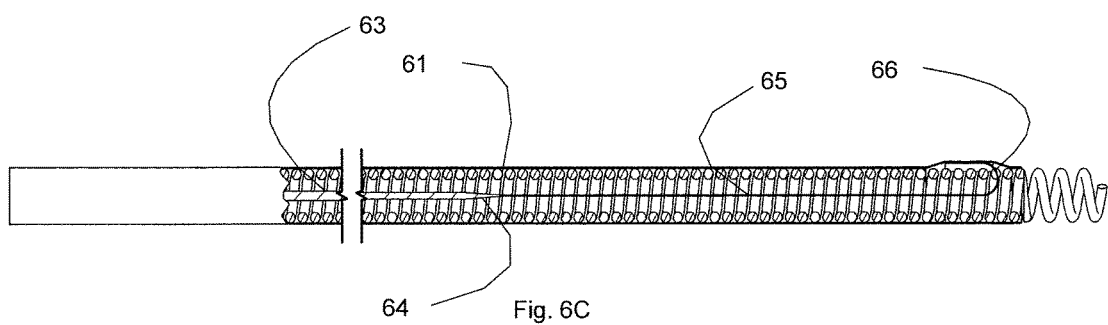
FIG. 6C (sheet 11/14) is a blow-up sectional view of the apparatus components inside the distal portion of the catheter shaft and inside the expandable element showing additional details of the actively deflectable mandrel invention embodiment of FIGS. 6A and 6B.
Figure 6D:
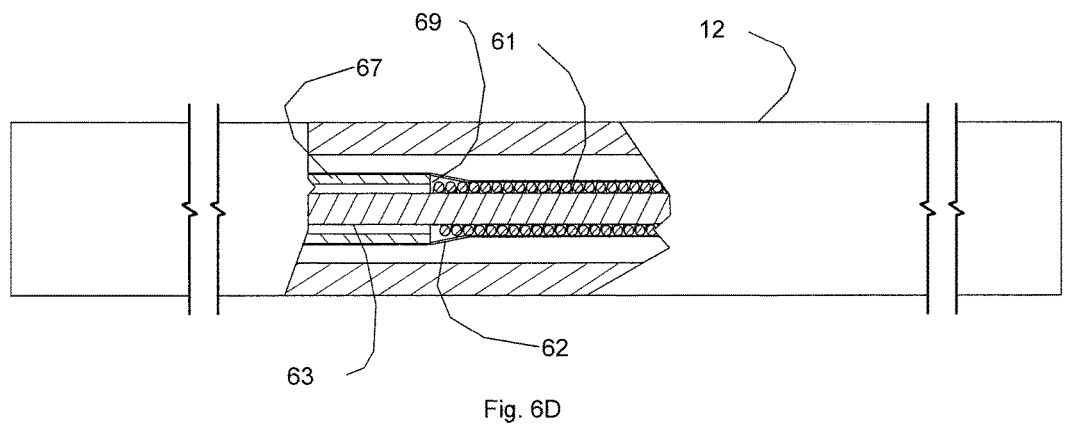
FIG. 6D (sheet 11/14) is a blow-up sectional view of the apparatus components inside the catheter shaft showing details of the juncture between a tube element and a deflectable spring element for the invention embodiment of FIGS. 6A, 6B and 6C.

In a preferred embodiment, the entire length of spring 61 is enveloped in a protective sheath, such as a polymer coating 62 (best seen in FIG. 6D). Also in a preferred embodiment, a distal portion of spring 61, for example a spring portion distal of the taper point 64, comprises coils having a spaced relationship (as better seen in FIG. 6C) relative to the more closely spaced coils along a proximal portion of spring 61. The greater spacing of spring coils along a more distal part of the spring adds greater flexibility/deflectability to the distal end of the assembly and also facilitates hooking the hooked end 66 of the mandrel between the coils.

FIG. 6B is an exploded, schematic sectional view of the proximal end of a catheter/expandable element assembly corresponding to the actively deflectable assembly tip embodiment of FIG. 6A. FIG. 6B is comparable to the configuration seen in FIGS. 1C and 1D showing a bifurcation assembly comprising an inflation arm 42 and a mandrel arm 44 with a male cap 48. FIG. 6B, however, shows a mandrel tensioning assembly 90 mounted proximally of the end of mandrel arm 44. Mandrel tensioning assembly 90 comprises two threadably-engaged tensioning elements—a cap extension element 91 and a mandrel pull screw 92.

Figure 7B:
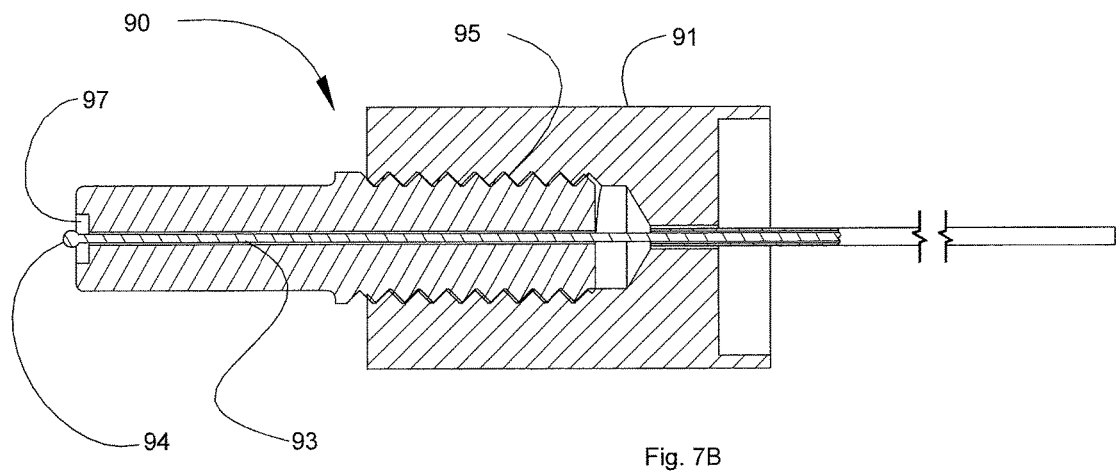
FIG. 7B (sheet 12/14) is a blow-up of the mandrel deflection mechanism seen in FIG. 6B at the proximal portion of the catheter assembly showing additional details of a proximal end configuration adapted for practicing the actively deflectable invention embodiment of FIGS. 6A to 6D.
Figure 7C:
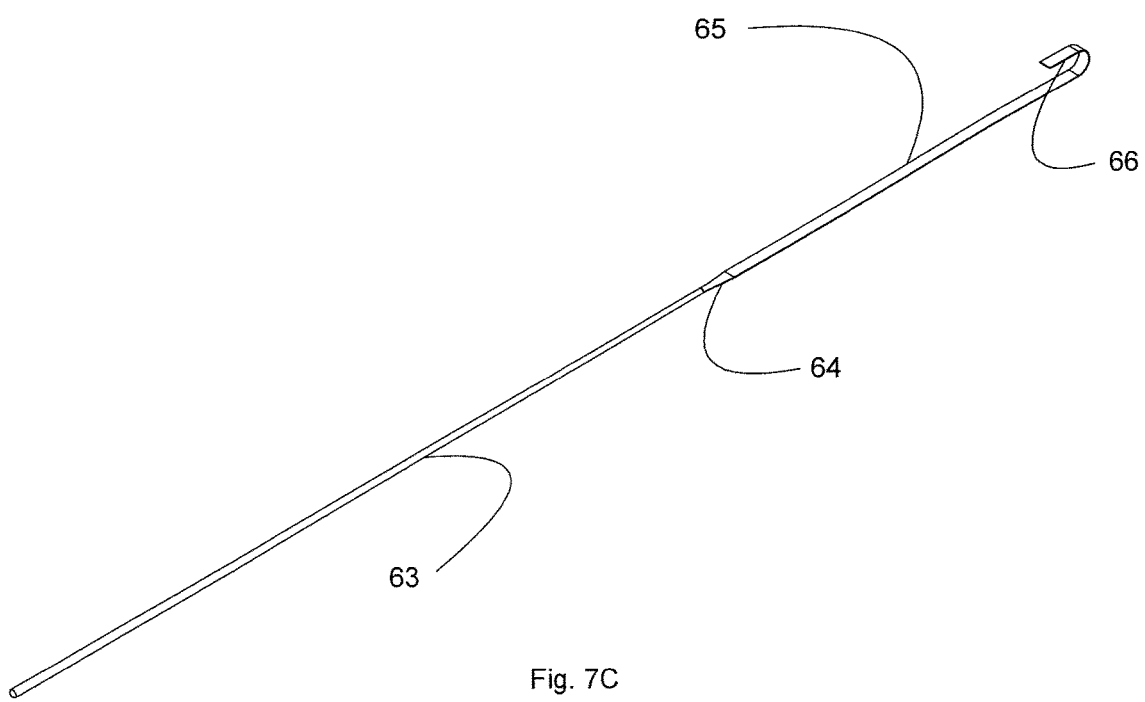
FIG. 7C (sheet 13/14) is an isolated isometric view of the distal portion of the mandrel/core wire as seen in FIG. 6C showing certain configuration details with greater clarity.

As better seen in the blow-up of FIG. 7B, proximal end 93 of the mandrel extends proximally through an axially aligned aperture in the cap 48 (see FIG. 6B), through an open channel in the center of the internally threaded cap extension 91, and along the hollow center axis of pull screw 92, and terminates in a geometrically enlarged feature, such as a ball end 94, beyond the proximal end of pull screw 92. As seen in FIGS. 6B and 7B, the proximal end of pull screw 92 may comprise a small central recess 97 to accommodate the enlarged proximal end of the mandrel. Pull screw 92 is sized and externally threaded to mate with internal threads in a recessed portion 95 of cap extension 91. As a result of this configuration, rotating pull screw 92 in an appropriate clockwise or counterclockwise direction (illustrated by a rotation arrow in FIG. 6B) results in withdrawing pull screw 92 from the threaded interior 95 of cap extension 91.

As pull screw 92 retracts from cap extension 91 in a proximal direction, it applies axial tensioning to the proximal end 93 of the mandrel and simultaneously to the distal end 63 (FIG. 6A) of the mandrel. The result of pulling the mandrel in a proximal direction by rotating pull screw 92 is to cause the hooked end 66 of the mandrel to deflect the end of the mandrel and of the spring 61, as indicated by the dotted lines in FIG. 7A. As a consequence, the entire distal tip of the catheter/expanded element assembly is caused to deflect.

Rotating the pull screw 92 in an opposite direction (so as to advance pull screw 92 into the recessed internally-threaded section 95 of cap extension 91) releases the axial tensioning of the mandrel and allows the deflected tip portion of the assembly to return (under action of spring 61) to its pre-deflected axial alignment. Because the proximal end 93 of the mandrel is not attached to cap extension 91 or to pull screw 92, but rather rests freely in the axial channel running through these elements, the mandrel is not rotated by rotation of pull screw 92. At the same time, because the enlarged head 94 of the mandrel is larger than the diameter of the axial channel, the proximal end of the mandrel cannot be pulled into the interior of pull screw 92.

FIG. 6C is an isolated, schematic sectional blow-up of the mandrel 63 and spring 61 inside the balloon 16 as shown in FIG. 6A. FIG. 6C provides a better illustration of the tapering mandrel, tapering to taper point 64, and the hooked end 66 engaging the distal coils of spring 61.

FIG. 6D is an isolated, schematic partial-sectional blow-up of the interior of the catheter shaft 12 at the point where a proximally-located tube or rod element 67 inside the catheter shaft forms a tube-spring juncture 69 with the distally-located deflection spring 61. In a preferred embodiment, element 67 and spring 61 are housed in a polymeric sheath 62 that separates these elements from inflation fluid passing through the catheter shaft. The tube element 67 and spring 61 may be maintained in adjacent axial alignment at juncture 69 because both are encased in the polymeric sheath 62, and also because of the axial tensioning caused by the hooked end 66 of the mandrel engaging the coils of spring 61.

Figure 8A:
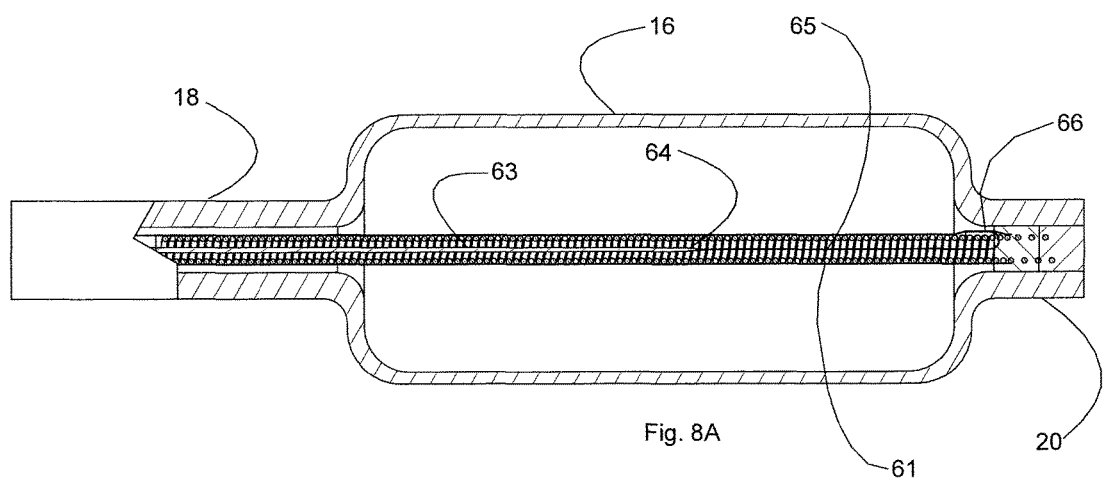
FIG. 8A (sheet 14/14) is an exploded, schematic sectional view of the distal end (i.e., that portion inside the circle A) of the assembly illustrated in FIG. 1A showing another alternative invention embodiment for configuring the distal end of the assembly to provide a passively deflectable expandable element configuration.
Figure 8B:
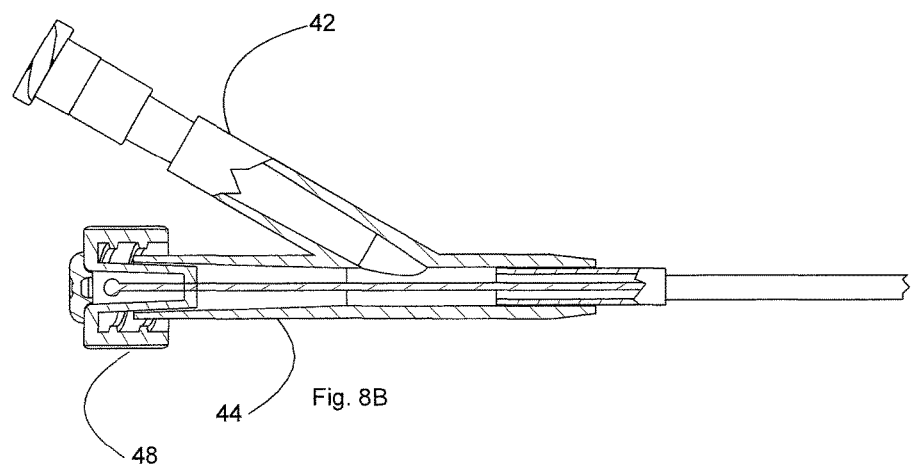
FIG. 8B (sheet 14/14) is an exploded, schematic sectional view of the proximal end (i.e., that portion inside the circle B) of the assembly illustrated in FIG. 1A showing a proximal end configuration consistent with the passively deflectable configuration of FIG. 8A.

FIGS. 8A and 8B illustrate an alternative invention embodiment designed to improve the flexibility of the distal end of a catheter/expandable element assembly, but without the active deflectability of the embodiment shown in FIGS. 6A to 6D and FIGS. 7A to 7C. FIG. 8A is generally comparable to FIG. 6A, except in FIG. 8A there is no reason to have a coil separation in the spring coils along the distal portion of spring 61, as was preferred in FIG. 6A. The preference for a coil separation in the embodiment of FIG. 6A was to better accommodate active deflectability of the tip, which is not a feature of the embodiment of FIG. 8A.

FIG. 8B shows the proximal end of an assembly corresponding to FIG. 8A. FIG. 8B is generally comparable to FIG. 6B, except the embodiment of FIGS. 8A and 8B does not require the mandrel tensioning mechanism 90 of FIG. 6B. Instead, FIG. 8B more closely resembles FIG. 1D, the main difference from FIG. 1D being in the configuration that includes the proximal end of the sheath-covered tube (see FIG. 6D) that forms a juncture with the distally-located spring 61, as described more completely above with reference to FIGS. 6C and 6D.

It will be apparent to those skilled in the art that other changes and modifications may be made in the above-described systems, apparatus and methods without departing from the scope of the invention herein, and it is intended that all matter contained in the above description shall be interpreted in an illustrative and not a limiting sense.

The invention claimed is:

1. A catheter/expandable element assembly with proximal and distal assembly ends for medical applications comprising a catheter shaft having a long axis and proximal and distal catheter portions, an expandable element comprising a conforming balloon portion suitable for treating vertebral fractures and related Kyphoplasty-type procedures with a balloon interior and also comprising a proximal neck portion bonded at a bond juncture to the distal catheter portion wherein a proximal end of the proximal neck portion is bonded to a terminal end of the distal catheter portion, and a fluid passageway extending from the proximal catheter portion to the balloon interior, the assembly being characterized by one or more of the following features:

(a) the expandable element comprises a conforming balloon suitable for Kyphoplasty-type procedures which can be stretched, folded and/or wrapped to a maximum diameter of less than 0.092 inches before inflation of the balloon portion and also following inflation and subsequent deflation of the balloon portion after a treatment procedure;

(b) the assembly includes both a stretched, folded and/or wrapped balloon portion and a bond juncture between the catheter shaft and the proximal neck portion that will fit through the interior of a standard 11-gauge medical cannula before inflation of the balloon portion and also following inflation and subsequent deflation of the balloon portion after a treatment procedure;

(c) the assembly includes both a stretched, folded and/or wrapped balloon portion and a bond juncture between the catheter shaft and the proximal neck portion that will fit through the interior of a standard 11-gauge medical cannula before inflation of the balloon portion and also following inflation and subsequent deflation of the balloon portion after a treatment procedure without the use of any lubricant or similar friction-reducing substance;

(d) the expandable element can be stretched, folded and/or wrapped to sufficiently reduce the cross-sectional profile of the assembly before inflation of the balloon portion and also following inflation and subsequent deflation of the balloon portion after a treatment procedure to be compatible with the use of a narrow gauge cannula;

(e) the expandable element can be stretched folded and/or wrapped to sufficiently reduce the cross-sectional profile of the assembly before inflation of the balloon portion and also following inflation and subsequent deflation of the balloon portion after a treatment procedure to be compatible with the use of an 11-gauge or smaller-diameter cannula;

(f) the catheter shaft is a single lumen catheter shaft and the assembly includes both a stretched, folded and/or wrapped balloon portion and a bond juncture between the catheter shaft and the proximal neck portion that will fit through the interior of a standard 11-gauge medical cannula before inflation of the balloon portion and also following inflation and subsequent deflation of the balloon portion after a treatment procedure;

(g) the proximal neck portion is butt-jointed by an adhesive bonding procedure, a solvent bonding procedure and/or a thermal bonding procedure to a terminal end of the distal catheter portion;

(h) the expandable element comprises a distal neck portion having a sealed tip, and the sealed tip contains the only radiopaque marker along the expandable element;

(i) the expandable element comprises one or more bands of a radiopaque material under the balloon portion with or without radiopaque material at a distal tip of the expandable element;

(j) the assembly comprises a feature selected from features (a) to (g), and additionally comprises a floating mandrel element that extends through the distal catheter portion, and through the expandable element to an interior distal portion of the expandable element;

(k) the assembly comprises a feature selected from features (a) to (g), and additionally comprises a floating mandrel element that extends through the distal catheter portion, and through the expandable element to an interior distal portion of the expandable element and further wherein the mandrel element has a free, unbonded proximal mandrel end and a distal mandrel end bonded to the interior distal portion of the expandable element;

(l) the assembly comprises a feature selected from features (a) to (g), and additionally comprises a catheter bifurcation assembly at a proximal end of the catheter shaft;

(m) the assembly comprises a feature selected from features (a) to (g), and additionally comprises a catheter bifurcation assembly at the proximal assembly end having an inflation arm portion in fluid communication with the balloon interior;

(n) the assembly comprises a feature selected from features (a) to (g), and additionally comprises a sleeve section of the distal catheter portion that accommodates limited axial movement of a mandrel inside the sleeve section and the free, unbonded proximal end of the mandrel is of an enlarged size such that the proximal end of the mandrel is retained in the sleeve;

(o) the assembly comprises a feature selected from features (a) to (g), and additionally comprises a floating mandrel element for actively or passively applying axial and/or rotational forces to the balloon portion, following a balloon inflation and treatment procedure and subsequent deflation but prior to withdrawing the balloon portion, causing the balloon portion to stretch axially and/or to wrap at least in part around the mandrel element to reduce the profile of the balloon portion and thereby facilitate a withdrawal procedure;

(p) the assembly comprises a feature selected from features (a) to (g), and additionally comprises a floating mandrel element that extends through the distal catheter portion, and through the expandable element to an interior distal wall portion of the expandable element, and further wherein a distal mandrel end is bonded to the distal end of the assembly and an unbonded proximal mandrel end has an enlarged geometrical feature such that the mandrel can move axially along or parallel to the long axis of the catheter shaft but only within an assembly portion that is bounded by a mandrel retaining structure;

(q) the assembly additionally comprises a mandrel element that extends through the distal portion of the catheter shaft, and through the expandable element, to an interior distal end of the assembly, wherein a distal portion of the mandrel element beginning inside the catheter shaft and extending through the expandable element is of a reduced diameter relative to a proximal portion of the mandrel element;

(r) the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion;

(s) the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion, and additionally comprising an elongated spring element with spring coils that surround the mandrel element beginning at a location proximal of the expandable element and extending into and through the expandable element to a distal tip of the expandable element where the distal end of the spring is bonded, and furthermore wherein the hooked mandrel tip engages one or more of the spring coils;

(t) the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion, and additionally comprising an elongated spring element with spring coils that surround the mandrel element beginning at a location proximal of the expandable element and extending into and through the expandable element to a distal tip of the expandable element where the distal end of the spring is bonded, and furthermore wherein the hooked mandrel tip engages one or more of the spring coils, and also wherein there is greater spacing between adjacent spring coils along a distal spring portion than along a proximal spring portion;

(u) the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion, and additionally comprising an elongated spring element with spring coils that surround the mandrel element beginning at a location proximal of the expandable element and extending into and through the expandable element to a distal tip of the expandable element where the distal end of the spring is bonded, and furthermore wherein the hooked mandrel tip engages one or more of the spring coils, and also wherein the spring is covered by a polymeric sleeve;

(v) the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion, and additionally comprising an elongated spring element with spring coils that surround the mandrel element beginning at a location proximal of the expandable element and extending into and through the expandable element to a distal tip of the expandable element where the distal end of the spring is bonded, and furthermore wherein the hooked mandrel tip engages one or more of the spring coils, and also wherein the mandrel can be axially tensioned so as to compress the spring where the hooked mandrel tip engages the spring coils causing the distal end of the expandable element to deflect from an axial orientation while the mandrel is axially tensioned; and, (w) the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion, and additionally comprising an elongated spring element with spring coils that surround the mandrel element beginning at a location proximal of the expandable element and extending into and through the expandable element to a distal tip of the expandable element where the distal end of the spring is bonded, and furthermore wherein the hooked mandrel tip engages one or more of the spring coils, and also comprising a mandrel tensioning assembly consisting of two threadably-engaged mandrel tensioning elements whereby the threadably-engaged tensioning elements provide an axial channel in which one of the mandrel tensioning elements can slide such that rotating one tensioning element relative to the other causes one of the tensioning elements to move in a proximal direction relative to the second tensioning element thereby applying axial tensioning to the mandrel and causing deflection of the hooked mandrel tip and the distal tip of the expandable element while the axial tensioning is applied.

2. A system for carrying out a medical dilatation and/or a cavity creation, enlargement or treatment procedure at an internal body site comprising a catheter/expandable element assembly according to any combination of characterizing features of claim 1 in combination with an 11-gauge or smaller diameter cannula having a cannula interior for delivering the expandable element from outside the body, through the cannula interior, to the desired internal body site and, following a treatment procedure, for withdrawing the deflated expandable element from the body site through the cannula interior.

3. A system according to claim 2 wherein the cannula interior is free of any lubricant and also wherein no lubricant is applied to the catheter/expandable element assembly.

4. A method for carrying out a medical treatment that includes a dilatation and/or a cavity creation, enlargement or treatment procedure using a system according to claim 2, the method comprising the steps of: (A) positioning the cannula in a body location so that a distal end of the cannula is proximate to the intended treatment site; (B) inserting at least the expandable element portion of the assembly through the cannula interior to position the expandable element in the interior of a bone or body site without the use of any lubricants; (C) inflating the balloon portion of the expandable element inside the interior of the bone or body site to a size and/or inflation pressure and for a time sufficient to complete the treatment; (D) deflating the balloon portion of the expandable element; and, (E) withdrawing the expandable element including the deflated balloon portion of the assembly through the cannula interior without the use of any lubricants.

5. A method for carrying out a medical treatment that includes a dilatation and/or a cavity creation, enlargement or treatment procedure that is performed with an expandable conforming balloon using a catheter/expandable element assembly according to any combination of characterizing features of claim 1, the method comprising the steps of: (A) inserting at least the expandable element portion of the assembly through the interior of a previously-placed 11-gauge or smaller diameter cannula to position the expandable element including a distal tip of the expandable element in the interior of a bone or body site; (B) inflating the balloon portion of the expandable element inside the interior of the bone or body site to a size and/or inflation pressure and for a time sufficient to complete the treatment; (C) deflating the balloon portion of the expandable element; and (D) withdrawing the expandable element including the deflated balloon portion of the assembly through the interior of the 11-gauge or smaller diameter cannula.

6. A method according to claim 5 additionally comprising a step of stretching, folding and/or wrapping the balloon portion of the expandable element following step (C) and prior to step (D).

7. A method according to claim 5 wherein the assembly includes a mandrel and additionally comprising a step, between steps (A) and (C), of temporarily deflecting the distal tip of the expandable element out of alignment with the long axis of the catheter shaft by applying axial tensioning to a hooked mandrel distal tip that engages at least some of the coils of a coiled spring element surrounding the portion of the mandrel inside the expandable element, where the distal end of the spring element is bonded to the distal tip of the expandable element.

8. A method according to claim 7 further comprising a step, before step (D), of relaxing the axial tensioning of the mandrel and allowing the distal tip of the expandable element to return to alignment with the long axis of the catheter shaft by action of the spring element.

9. A method of manufacturing the assembly of claim 1 by bonding the terminal end of the distal catheter portion to the proximal end of the proximal neck portion, the method comprising the steps of butting the terminal end of the distal catheter portion against a similarly-sized proximal end of the proximal neck portion followed by an adhesive bonding procedure, a solvent bonding procedure or a thermal bonding procedure for securing the two abutting ends to one another thereby creating a fluid passageway through the interior of the catheter shaft and into the balloon portion of the expandable element.

10. A method of manufacturing an assembly according to claim 9 further including positioning a mandrel inside the assembly and providing a mandrel retention structure for restricted axial movement of the mandrel, the method also comprising the steps of bonding the distal end of the mandrel to the inside distal end of the expandable element and providing an unbonded proximal end of the mandrel with an enlarged geometrical feature that retains the mandrel inside a sleeve section of the assembly.

11. The method of claim 10 wherein the enlarged geometrical feature at the proximal end of the mandrel cannot pass through an aperture of the mandrel retention structure to retain the enlarged proximal end of the mandrel in the sleeve section.

12. An assembly according to claim 1 wherein the assembly additionally comprises a mandrel element that extends through the distal portion of the catheter shaft, and through the expandable element, to an interior distal end of the assembly, wherein a distal portion of the mandrel element beginning inside the catheter shaft and extending through the expandable element is of a reduced diameter relative to a proximal portion of the mandrel element.

13. An assembly according to claim 1 wherein the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion.

14. An assembly according to claim 1 wherein the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion, and additionally comprising an elongated spring element with spring coils that surround the mandrel element beginning at a location proximal of the expandable element and extending into and through the expandable element to a distal tip of the expandable element where the distal end of the spring is bonded, and furthermore wherein the hooked mandrel tip engages one or more of the spring coils.

15. An assembly according to claim 1 wherein the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion, and additionally comprising an elongated spring element with spring coils that surround the mandrel element beginning at a location proximal of the expandable element and extending into and through the expandable element to a distal tip of the expandable element where the distal end of the spring is bonded, and furthermore wherein the hooked mandrel tip engages one or more of the spring coils, and also wherein there is greater spacing between adjacent spring coils along a distal spring portion than along a proximal spring portion.

16. An assembly according to claim 1 wherein the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion, and additionally comprising an elongated spring element with spring coils that surround the mandrel element beginning at a location proximal of the expandable element and extending into and through the expandable element to a distal tip of the expandable element where the distal end of the spring is bonded, and furthermore wherein the hooked mandrel tip engages one or more of the spring coils, and also wherein the spring is covered by a polymeric sleeve.

17. An assembly according to claim 1 wherein the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion, and additionally comprising an elongated spring element with spring coils that surround the mandrel element beginning at a location proximal of the expandable element and extending into and through the expandable element to a distal tip of the expandable element where the distal end of the spring is bonded, and furthermore wherein the hooked mandrel tip engages one or more of the spring coils, and also wherein the mandrel can be axially tensioned so as to compress the spring where the hooked mandrel tip engages the spring coils causing the distal end of the expandable element to deflect from an axial orientation while the mandrel is axially tensioned.

18. An assembly according to claim 1 wherein the assembly additionally comprises a mandrel element that extends through the distal portion of the catheter shaft, and into the expandable element, wherein at least the portion of the mandrel element inside the expandable element tapers to a flattened distal mandrel end that terminates in an unbonded angled or hooked mandrel tip at a location proximate to the distal end of the balloon portion, and additionally comprising an elongated spring element with spring coils that surround the mandrel element beginning at a location proximal of the expandable element and extending into and through the expandable element to a distal tip of the expandable element where the distal end of the spring is bonded, and furthermore wherein the hooked mandrel tip engages one or more of the spring coils, and also comprising a mandrel tensioning assembly consisting of two threadably-engaged mandrel tensioning elements whereby the threadably-engaged tensioning elements provide an axial channel in which one of the mandrel tensioning elements can slide such that rotating one tensioning element relative to the other causes one of the tensioning elements to move in a proximal direction relative to the second tensioning element thereby applying axial tensioning to the mandrel and causing deflection of the hooked mandrel tip and the distal tip of the expandable element while the axial tensioning is applied.

19. A catheter/expandable element assembly with proximal and distal assembly ends for medical applications comprising:
- a catheter shaft having a long axis and proximal and distal catheter portions;
- an expandable element comprising a balloon portion suitable for treating vertebral fractures and related Kyphoplasty-type procedures with a balloon interior and also comprising a proximal neck portion bonded at a bond juncture to the distal catheter portion, wherein an outer diameter of the distal catheter portion and an outer diameter of the proximal neck portion at the bond juncture are substantially the same size so as to form a smooth, uninterrupted outer surface at the bond juncture and the balloon portion and the bond juncture can be passed through an 11-gauge or smaller diameter medical cannula before inflation of the balloon portion and also following inflation and subsequent deflation of the balloon portion after a treatment procedure;
- a fluid passageway extending from the proximal catheter portion through the distal catheter portion to the balloon interior; and,
- a floating mandrel that extends through the distal catheter portion and through the expandable element to a distal portion of the expandable element, wherein the floating mandrel comprises a distal mandrel end bonded to the expandable element and a free, unbonded proximal mandrel end whereby the floating mandrel has a limited range of axial movement along or parallel to the long axis of the catheter shaft.

20. An assembly according to claim 19 wherein the assembly has a maximum diameter of less than 0.092 inches at the bond juncture.

21. An assembly according to claim 19 wherein the fluid passageway has a generally circular cross-section with a fluid passageway diameter defined by an inner wall of the catheter shaft and wherein the fluid passageway diameter on either side of the bond juncture is substantially the same size as an inner diameter of the distal catheter portion at the bond juncture.

22. An assembly according to claim 19 wherein an inner diameter of the distal catheter portion, a diameter of the fluid passageway, and an inner diameter of the proximal neck portion at the bond juncture are substantially the same size.

23. An assembly according to claim 22 wherein the only catheter shaft is a single lumen catheter.

24. An assembly according to claim 19 wherein the distal catheter portion and the proximal neck portion are butt-jointed and bonded to each other at the bond juncture.

25. A catheter/expandable element assembly with proximal and distal assembly ends for medical applications comprising:
- a single catheter shaft having a long axis and proximal and distal catheter portions;
- an expandable element comprising a balloon portion suitable for treating vertebral fractures and related Kyphoplasty-type procedures with a balloon interior and also comprising a proximal neck portion butt jointed and bonded at a bond juncture to the distal catheter portion wherein the balloon portion and the bond juncture can be passed through an 11-gauge or smaller diameter medical cannula before inflation of the balloon portion and also following inflation and subsequent deflation of the balloon portion after a treatment procedure; and,
- a fluid passageway extending from the proximal catheter portion to the balloon interior,
- and further wherein an inner diameter of the distal catheter portion, a diameter of the fluid passageway, and an inner diameter of the proximal neck portion at the bond juncture are substantially the same size, and also wherein an outer diameter of the distal catheter portion and an outer diameter of the proximal neck portion at the bond juncture are substantially the same size so as to form a smooth, uninterrupted outer surface at the bond juncture.

26. An assembly according to claim 25 further comprising a floating mandrel that extends through the distal catheter portion and through the expandable element to a distal portion of the expandable element, wherein the floating mandrel comprises a distal mandrel end bonded to the expandable element and a free, unbonded proximal mandrel end.

27. An assembly according to claim 25 wherein the assembly has a maximum diameter of less than 0.092 inches at the bond juncture.

28. An assembly according to claim 25 wherein the only catheter shaft is a single lumen catheter.

* * * * *